US010052092B2

(12) United States Patent
Finley et al.

(10) Patent No.: US 10,052,092 B2
(45) Date of Patent: Aug. 21, 2018

(54) SUTURE ANCHOR RELOAD

(71) Applicant: Biomet Sports Medicine, LLC, Warsaw, IN (US)

(72) Inventors: Adam Finley, Winona Lake, IN (US); Kevin T. Stone, Winona Lake, IN (US); Daniel Norton, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 925 days.

(21) Appl. No.: 14/489,695

(22) Filed: Sep. 18, 2014

(65) Prior Publication Data

US 2015/0005820 A1    Jan. 1, 2015

Related U.S. Application Data

(63) Continuation-in-part of application No. 13/485,304, filed on May 31, 2012, now abandoned.

(51) Int. Cl.
| *A61B 17/04* | (2006.01) |
| *A61B 17/17* | (2006.01) |
| *A61B 17/34* | (2006.01) |
| *A61B 17/00* | (2006.01) |

(52) U.S. Cl.
CPC .......... *A61B 17/0401* (2013.01); *A61B 17/17* (2013.01); *A61B 17/0485* (2013.01); *A61B 17/3468* (2013.01); *A61B 2017/0053* (2013.01); *A61B 2017/0409* (2013.01); *A61B 2017/0416* (2013.01); *A61B 2017/0446* (2013.01); *A61B 2017/0458* (2013.01)

(58) Field of Classification Search
CPC ................ A61B 17/0401; A61B 17/17; A61B 2017/0458; A61B 2017/0053; A61B 17/3468; A61B 17/0485; A61B 2017/0416; A61B 2017/0446; A61B 2017/0409

See application file for complete search history.

(56) References Cited

U.S. PATENT DOCUMENTS

| 5,207,692 A | 5/1993 | Kraus et al. |
| 5,520,702 A | 5/1996 | Sauer et al. |
| 5,733,293 A | 3/1998 | Scirica et al. |
| 5,810,848 A | 9/1998 | Hayhurst |

(Continued)

FOREIGN PATENT DOCUMENTS

| EP | 0599772 A1 | 6/1994 |
| WO | WO-2013181373 A2 | 12/2013 |

OTHER PUBLICATIONS

"U.S. Appl. No. 13/485,304, Advisory Action dated Feb. 9, 2017", 3 pgs.

(Continued)

*Primary Examiner* — Katherine M Shi
*Assistant Examiner* — Michael Mendoza
(74) *Attorney, Agent, or Firm* — Schwegman Lundberg & Woessner, P.A.

(57) ABSTRACT

A suture anchor loading system for loading a suture anchor on a suture. The suture anchor loading system includes a first portion and a second portion defining a suture anchor receptacle therebetween. A superstructure is configured to retain the first and the second portions together. The suture anchor can be loaded onto the suture when the suture anchor is seated within the suture anchor receptacle.

20 Claims, 18 Drawing Sheets

(56) References Cited

U.S. PATENT DOCUMENTS

| | | | |
|---|---|---|---|
| 5,897,564 | A | 4/1999 | Schulze et al. |
| 6,425,900 | B1 | 7/2002 | Knodel et al. |
| 6,447,524 | B1 | 9/2002 | Knodel et al. |
| 6,572,626 | B1 | 6/2003 | Knodel et al. |
| 6,626,916 | B1 | 9/2003 | Yeung et al. |
| 6,773,438 | B1 | 8/2004 | Knodel et al. |
| 6,974,466 | B2 | 12/2005 | Ahmed et al. |
| 7,048,748 | B1 | 5/2006 | Ustuner |
| 7,160,314 | B2 | 1/2007 | Sgro et al. |
| 7,485,124 | B2 | 2/2009 | Kuhns et al. |
| 7,615,061 | B2 * | 11/2009 | White ............... A61B 17/0401 289/17 |
| 7,645,286 | B2 | 1/2010 | Catanese, III et al. |
| 7,749,250 | B2 | 7/2010 | Stone et al. |
| 7,758,594 | B2 | 7/2010 | Lamson et al. |
| 7,758,612 | B2 | 7/2010 | Shipp |
| 7,896,891 | B2 | 3/2011 | Catanese, III et al. |
| 7,905,893 | B2 | 3/2011 | Kuhns et al. |
| 8,128,657 | B2 | 3/2012 | Shiono et al. |
| 8,157,815 | B2 | 4/2012 | Catanese, III et al. |
| 8,236,011 | B2 | 8/2012 | Harris et al. |
| 8,267,963 | B2 | 9/2012 | Williams |
| 8,398,657 | B2 | 3/2013 | Sauer |
| 2005/0288711 | A1 | 12/2005 | Fallin et al. |
| 2006/0282081 | A1 | 12/2006 | Fanton et al. |
| 2007/0203508 | A1 | 8/2007 | White et al. |
| 2007/0276365 | A1 | 11/2007 | Song et al. |
| 2008/0243143 | A1 | 10/2008 | Kuhns et al. |
| 2008/0275474 | A1 * | 11/2008 | Martin ............... A61B 17/0401 606/146 |
| 2010/0312258 | A1 | 12/2010 | Shipp |
| 2011/0071556 | A1 | 3/2011 | Shipp |
| 2011/0270280 | A1 | 11/2011 | Saliman |
| 2011/0306989 | A1 | 12/2011 | Darois et al. |
| 2012/0290005 | A1 | 11/2012 | Martin et al. |
| 2013/0023930 | A1 | 1/2013 | Stone et al. |
| 2013/0325063 | A1 | 12/2013 | Norton et al. |
| 2014/0257314 | A1 | 9/2014 | Brown et al. |

OTHER PUBLICATIONS

"U.S. Appl. No. 13/485,304, Final Office Action dated May 14, 2015", 16pgs.
"U.S. Appl. No. 13/485,304, Final Office Action dated Nov. 9, 2016", 16 pgs.
"U.S. Appl. No. 13/485,304, Non Final Office Action dated Oct. 6, 2014", 14 pgs.
"U.S. Appl. No. 13/485,304, Response filed Jan. 6, 2015 to Non Final Office Action dated Feb. 4, 2016", 15 pgs.
"U.S. Appl. No. 13/485,304, Response filed Jan. 6, 2015 to Non Final Office Action dated Oct. 6, 2014", 19 pgs.
"U.S. Appl. No. 13/485,304, Response filed May 30, 2014 to Restriction Requirement dated Mar. 31, 2014", 1 pg.
"U.S. Appl. No. 13/485,304, Response filed Aug. 4, 2016 to Non Final Office Action dated Feb. 4, 2016", 12 pgs.
"U.S. Appl. No. 13/485,304, Response filed Aug. 14, 2015 to Final Office Action dated May 14, 2015", 15 pgs.
"U.S. Appl. No. 13/485,304, Response filed Dec. 29, 2016 to Final Office Action dated Nov. 9, 2016", 14 pgs.
"U.S. Appl. No. 13/485,304, Restriction Requirement dated Mar. 31, 2014", 8 pgs.
"European Application Serial No. 13728293.5, Communication Pursuant to Article 94(3) EPC dated Nov. 17, 2016", 4 pgs.
"European Application Serial No. 13728293.5, Office Action dated Jan. 30, 2015", 2 pgs.
"European Application Serial No. 13728293.5, Response Filed Mar. 27, 2017 to Communication Pursuant to Article 94(3) EPC dated Nov. 17, 2016", 14 pgs.
"European Application Serial No. 13728293.5, Response filed Aug. 7, 2015 to Office Action dated Jan. 30, 2015", 11 pgs.
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labial Repair," brochure. Biomet Sports Medicine (Apr. 2011) 12 sheets.
International Search Report and Written Opinion dated Jan. 14, 2014 for PCT/US2013/043333 claiming benefit of U.S. Appl. No. 13/485,304, filed May 31, 2012.
Invitation to Pay Additional Fees and, where Applicable, Protest Fee mailed Sep. 12, 2013 for PCT/US2013/043333 claiming benefit of U.S. Appl. No. 13/485,304, filed May 31, 2012.
International Preliminary Report on Patentability and Written Opinion dated Dec. 11, 2014 for PCT/US2013/043333 claiming benefit of U.S. Appl. No. 13/485,304, filed May 31, 2012.

* cited by examiner

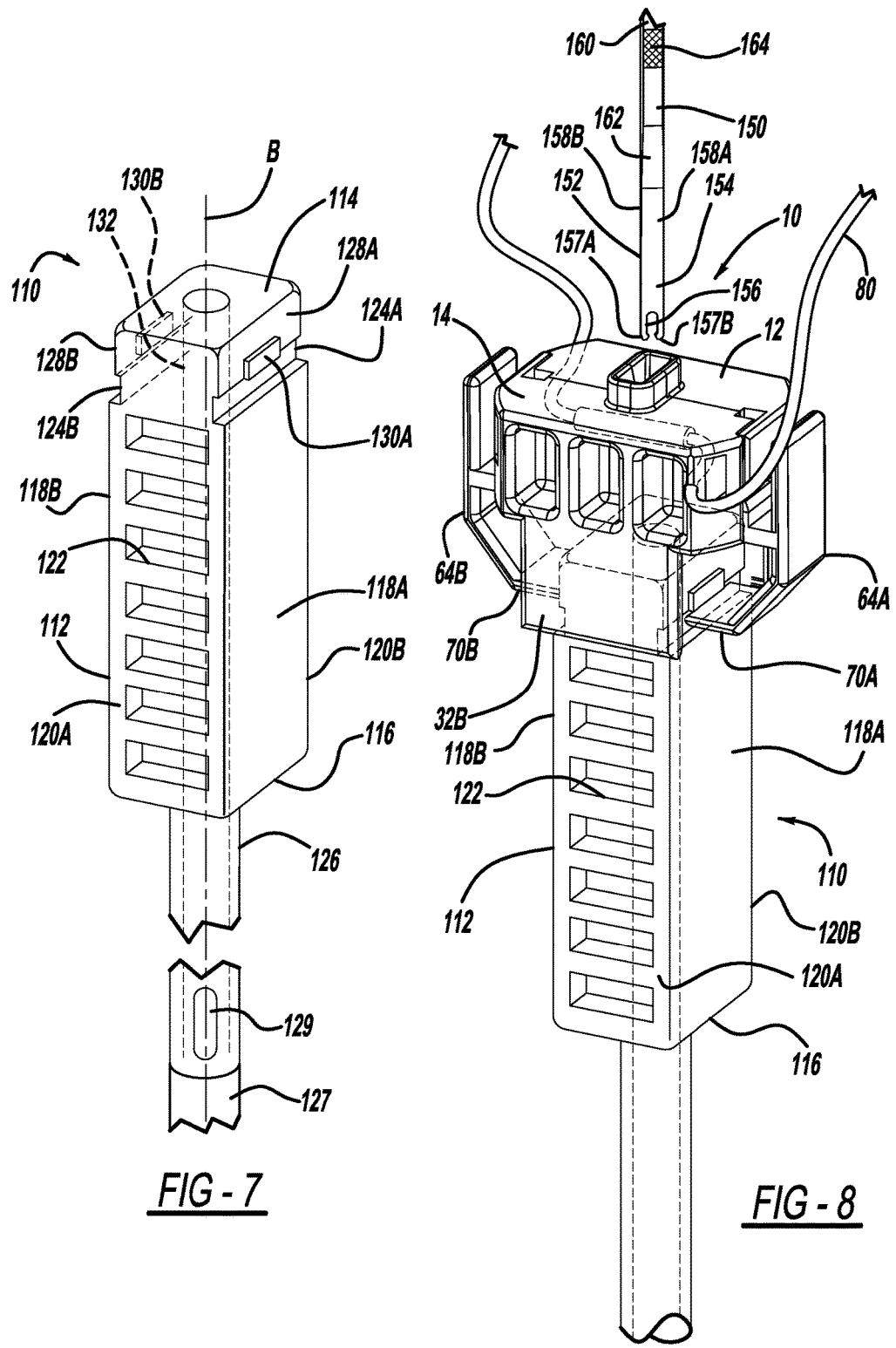

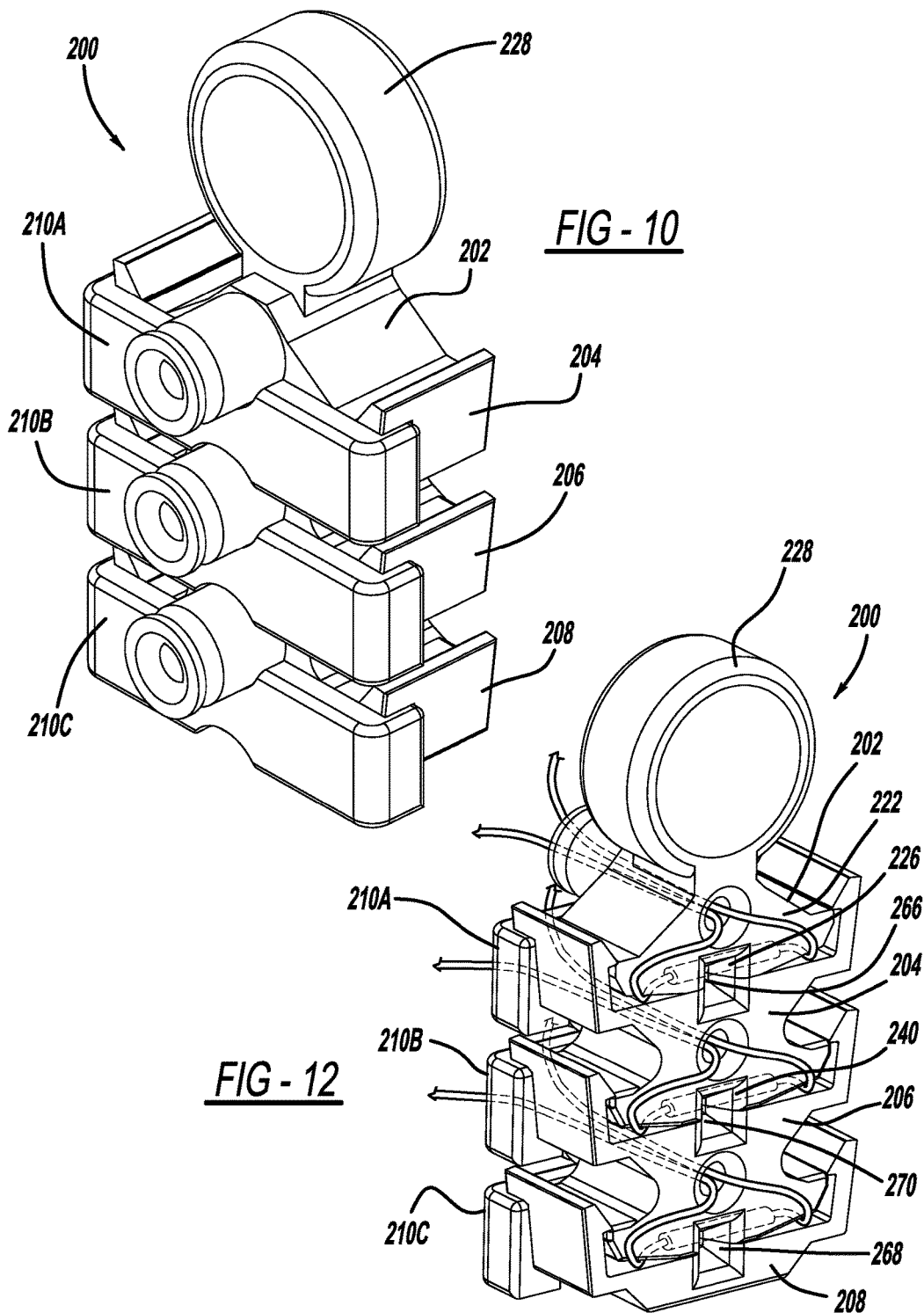

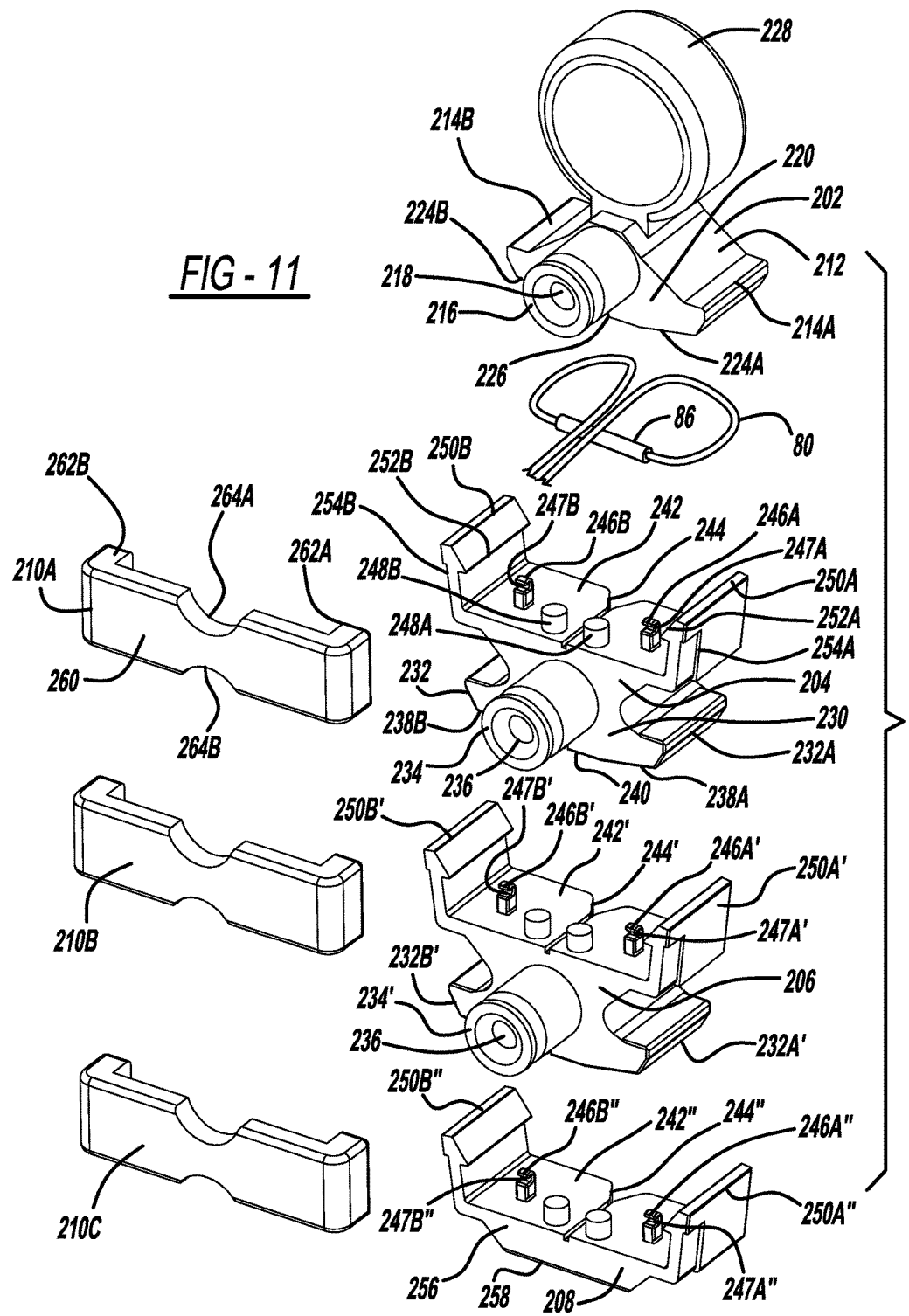

US 10,052,092 B2

SUTURE ANCHOR RELOAD

CROSS-REFERENCE TO RELATED APPLICATIONS

This application is a continuation-in-part of U.S. patent application Ser. No. 13/485,304 filed on May 31, 2012, the entire disclosure of which is incorporated herein by reference.

FIELD

The present disclosure relates to a suture anchor reload device and method.

BACKGROUND

This section provides background information related to the present disclosure which is not necessarily prior art.

To implant a suture anchor at an implant site, an inserter is often used. Any suitable inserter can be used, such as the inserter offered by Biomet, Inc. for use with its Jugger-Knot™ soft anchor. The suture anchor, such as the Jugger-Knot™ anchor by Biomet, Inc., is typically pre-loaded on the inserter because it may be inconvenient and difficult to load in the operating room. After the suture anchor is implanted, the inserter is typically disposed of. Thus, a different inserter is used for each suture anchor, which can increase cost and waste. A device for quickly and easily reloading a suture anchor onto an inserter would make it possible to use a single inserter to implant multiple suture anchors.

SUMMARY

This section provides a general summary of the disclosure, and is not a comprehensive disclosure of its full scope or all of its features.

The present teachings provide for a suture anchor loading system for loading a suture anchor on a suture. The suture anchor loading system includes a first portion and a second portion defining a suture anchor receptacle therebetween. A superstructure is configured to retain the first and the second portions together. The suture anchor can be loaded onto the suture when the suture anchor is seated within the suture anchor receptacle.

The present teachings further provide for a suture anchor loading assembly for loading a suture anchor on a suture. The suture anchor loading assembly includes a first portion and a second portion defining a suture anchor receptacle and an inserter receptacle therebetween. The suture anchor receptacle intersects the inserter receptacle. A superstructure defines a receptacle configured to receive the first and the second portions therein and retain the first and the second portions together. A suture anchor threading assembly includes a handle, a suture capture rod configured to receive the suture anchor thereon, and a suture capture portion. The suture capture rod having the suture anchor thereon is seated within the suture anchor receptacle. An inserter is seated in both the inserter receptacle and the suture anchor receptacle such that the inserter is coupled to the suture anchor. Withdrawal of the suture anchor threading assembly out from within the suture anchor receptacle pulls the suture capture portion with the suture coupled thereto through the suture anchor to thread the suture through the suture anchor.

The present teachings also provide for a method for loading a suture anchor onto a suture using a suture anchor loading assembly including a first portion and a second portion defining therebetween a suture anchor receptacle and an inserter receptacle intersecting the suture anchor receptacle. The method includes the following: inserting an inserter into the inserter receptacle and into the suture anchor receptacle to couple the inserter with the suture anchor; coupling the suture to a suture capture portion of a suture capture rod; withdrawing the suture capture rod out from within the suture anchor receptacle to thread the suture through the suture anchor; and advancing the inserter further into the inserter receptacle to force the first portion and the second portion apart and break the superstructure.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 7 is a perspective view of a drill guide for use with the suture anchor reload assembly of FIG. 1;

FIG. 8 is a perspective view of the suture anchor reload assembly in cooperation with the drill guide;

FIG. 10 is a perspective view of another suture anchor reload assembly according to the present teachings;

FIG. 11 is an exploded view of the assembly of FIG. 10;

FIG. 12 is a perspective view of the assembly of FIG. 10 with a plurality of sutures mounted thereto;

Corresponding reference numerals indicate corresponding parts throughout the several views of the drawings.

DETAILED DESCRIPTION

Example embodiments will now be described more fully with reference to the accompanying drawings.

Figure 1:
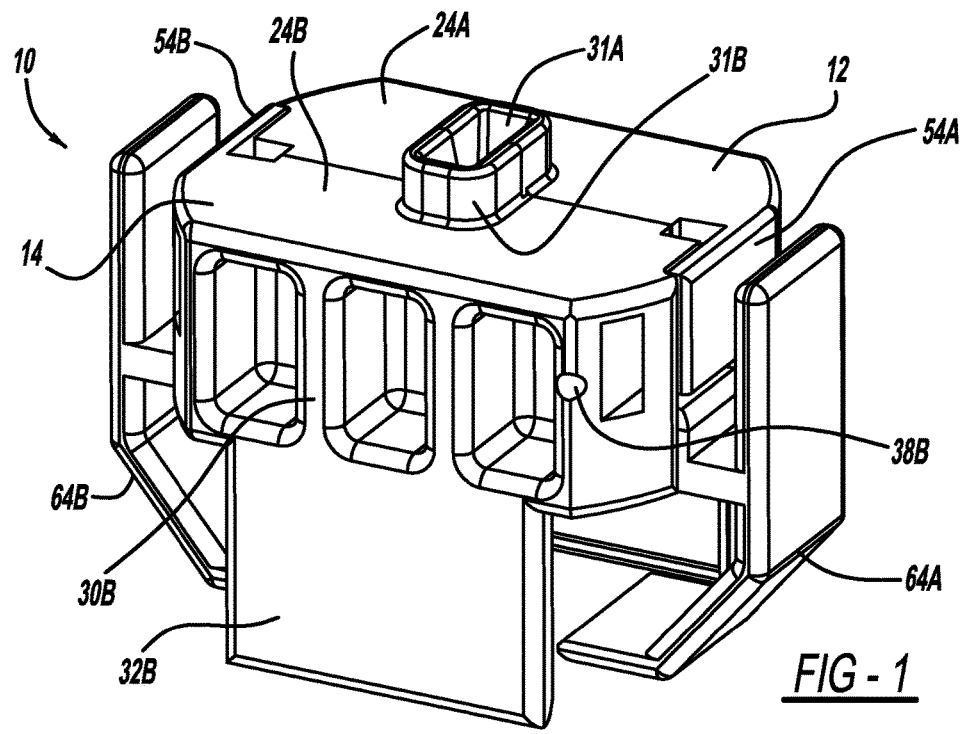
FIG. 1 is a perspective view of a suture anchor reload assembly according to the present teachings.
Figure 2:
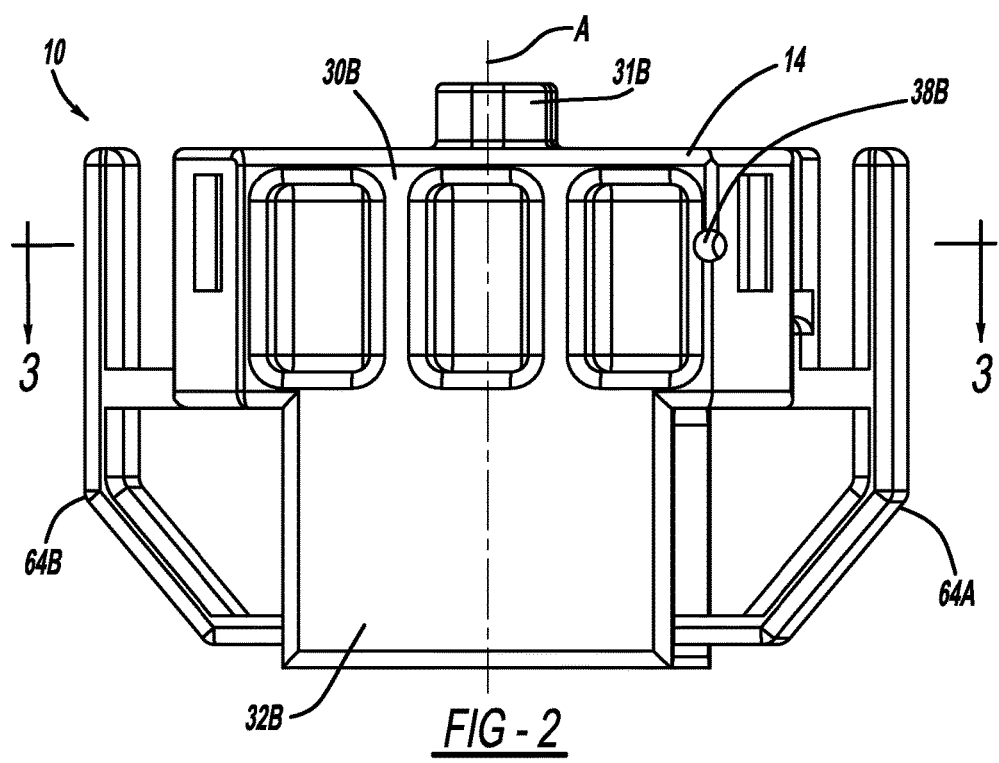
FIG. 2 is a side view of the reload assembly of FIG. 1.
Figure 3:
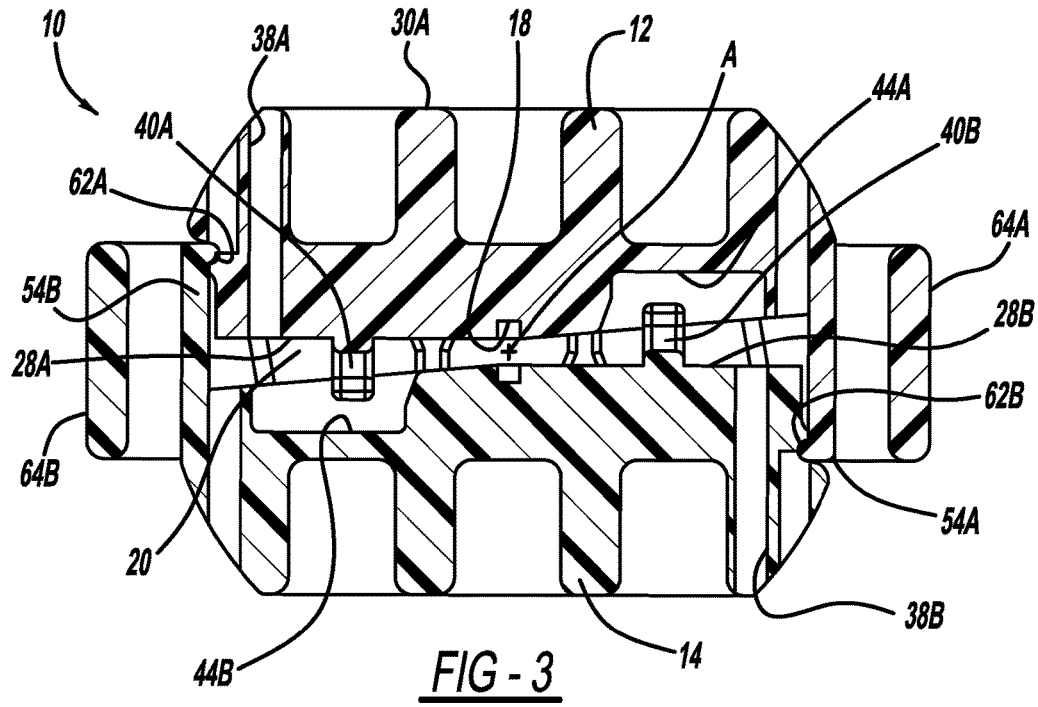
FIG. 3 is a cross-sectional view of the reload assembly taken along line 3-3 of FIG. 2.

With initial reference to FIGS. 1-3, a suture anchor reload assembly is generally illustrated at reference numeral 10. The reload assembly 10 generally includes a first portion or half 12 and a second portion or half 14, which can be substantially similar to one another, or identical as illustrated, to facilitate manufacturing and reduce costs. The first and the second halves 12 and 14 connect together to define, for example, an inserter receptacle 18 and a suture anchor cavity 20 (FIG. 3).

Figure 4:
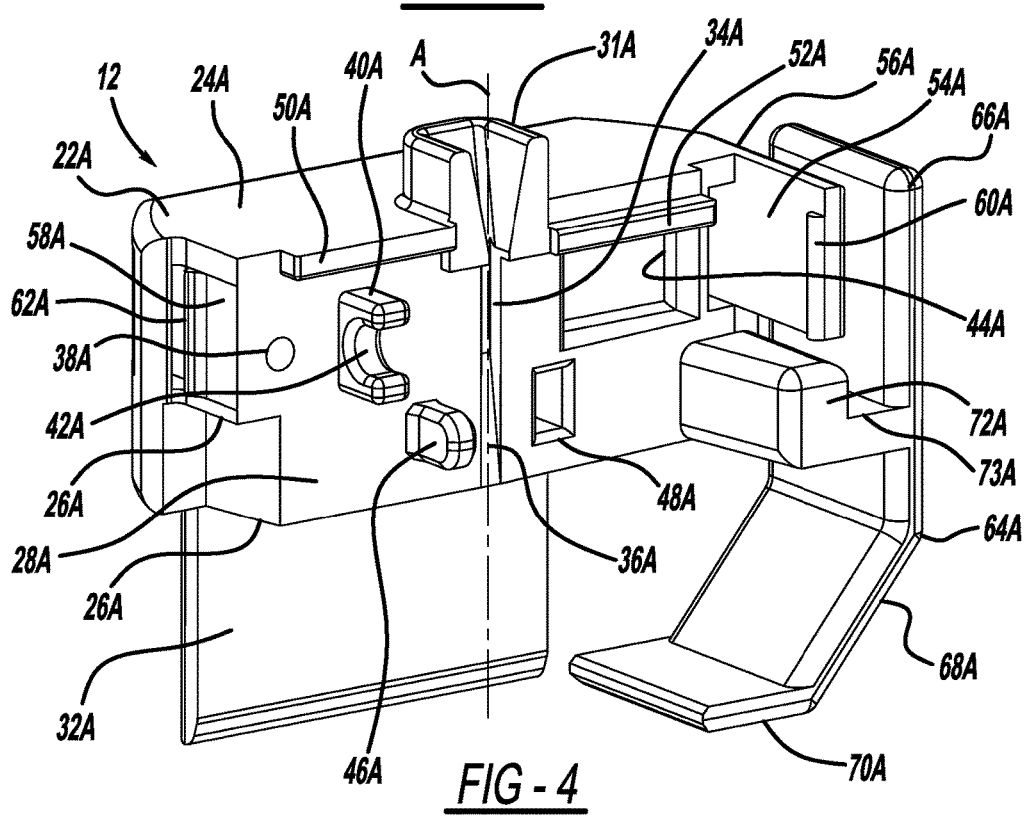
FIG. 4 is a perspective view of a first half of the reload assembly of FIG. 1.

With additional reference to FIGS. 4-6, features of the first half 12 will be described. Because the first half 12 and the second half 14 are identical, the description of the first half 12 also applies to the second half 14. To distinguish between the first half 12 and the second half 14, features of the first half 12 are designated with the letter "A" and features of the second half 14 are designated with the letter "B." While the first and the second halves 12 and 14 are described as separating along The first half 12 generally includes a main body 22A having a top surface 24A, a bottom surface 26A, an inner surface 28A, and an outer surface 30A. The top surface 24A and the bottom surface 26A are generally planar and extend parallel to one another. The top surface 24A is opposite to the bottom surface 26A and the inner surface 28A is opposite to the outer surface 30A. The inner surface 28A of the first half 12 and the inner surface 28B of the second half 14 generally define the suture anchor cavity 20. The outer surface 30A is overall generally planar and the inner surface 28A is generally concave with respect to the outer surface 30A, thereby defining the suture anchor cavity 20 as generally tapered outward in opposite directions from a longitudinal axis A of the suture anchor reload assembly 10. While the first and the second halves 12 and 14 are described as separating along a longitudinal axis extending a length of the suture cavity 20, the suture anchor reload assembly 10 can be configured such that the suture anchor reload assembly 10 separates along a line perpendicular to the longitudinal axis of the suture cavity 20. The suture anchor reload assembly 10 can also be monolithic.

Extending from the top surface 24A is an inserter guide flange 31A, which is generally U-shaped. Extending from the bottom surface 26A at the outer surface 30A is an alignment flange 32A, which facilitates alignment of the reload assembly 10 with a cannula or guide, such as a drill guide, as further described herein.

The inner surface 28A defines an inserter passageway or slot 34A, which extends from the U-shaped inserter guide flange 31A to the bottom surface 26A. The inserter passageway 34A is generally at a midpoint of the inner surface 28A and extends alongside of the longitudinal axis A (FIG. 4). The inserter passageway 34A includes an angled surface 36A proximate to the bottom surface 26A. The angled surface 36A begins at about a mid-point of the inserter passageway 34A and extends to the bottom surface 26A. The angled surface 36A is sloped along its length such that the angled surface 36A is about planar with the inner surface 28A where the inner surface 28A meets the bottom surface 26A.

The main body 22A defines a suture aperture 38A, which extends in a direction generally transverse to the longitudinal axis A between the inner surface 28A and the outer surface 30A and is about halfway between the top surface 24A and the bottom surface 26A. The suture aperture 38A has a generally circular cross-section. At the inner surface 28A, the suture aperture 38A is aligned with a suture holding member or suture alignment guide 40A, which is generally a flange that extends out from the inner surface 28A and defines a generally U-shaped guide surface 42A. The suture alignment guide 40A is between the suture aperture 38A and the inserter passageway 34A. Aligned with the suture aperture 38A and the suture alignment guide 40A, and at a side of the inserter passageway 34A opposite to the suture aperture 38A and the suture alignment guide 40A, is a suture alignment guide receptacle 44A. The receptacle 44A is defined by, and recessed within, the inner surface 28A to accommodate the suture alignment guide 40B of the second half 14 of the suture anchor reload assembly 10.

An alignment flange 46A for aligning the first half 12 with the second half 14 extends out from the inner surface 28A on the same side of the inserter passageway 34A as the suture alignment guide 40A. The alignment flange 46A is closer to the bottom surface 26A than the suture alignment guide 40A is. Aligned with the alignment flange 46A on an opposite side of the inserter passageway 34A is an alignment flange receptacle 48A, which is recessed within and defined by the inner surface 28A. The alignment flange receptacle 48A is sized and shaped to receive the alignment flange 46B of the second half 14 when the first half 12 is connected to the second half 14, as further described herein.

Extending from the inner surface 28A proximate to the top surface 24A are an upper spacing tab 50A and a lower spacing tab 52A. The upper spacing tab 50A and the lower spacing tab 52A are arranged on opposite sides of the inserter passageway 34A. The upper spacing tab 50A is aligned with the top surface 24A and the lower spacing tab 52B is offset from the top surface 24A a distance approximately equal to a thickness of the upper spacing tab 50A to accommodate the upper spacing tab 50B thereon when the first half 12 and the second half 14 are coupled together. The upper spacing tab 50A and the lower spacing tab 52B extend from the inner surface 28A to a distance less than either the suture alignment guide 40A or the alignment flange 46A. As further described herein, when the first half 12 and the second half 14 of the reload assembly 10 are coupled together, the upper spacing tab 50A and the lower spacing tab 52B extend to a distance sufficient to space the inner surface 28A from the inner surface 28B and define the suture anchor cavity 20 therebetween.

A flexible locking tab or coupling device 54A extends from the main body 22A generally at first side surface 56A of the main body 22A, which is opposite to a second side surface 58A. The locking tab 54A extends in a direction generally perpendicular to the inner surface 28A. At an end of the locking tab 54A opposite to the inner surface 28A is a coupling flange 60A. At the second side surface 58A is a locking tab coupling ridge 62A, which protrudes from the second side surface 58A. The locking tab coupling flange 60A is configured to mate with the coupling ridge 62B of the second half 14 and the coupling flange 60B is configured to mate with the coupling ridge 62A to secure the first half 12 of the reload assembly to the second half 14 of the reload assembly, as further described herein.

The first half 12 further includes a flexible drill guide connection flange or coupling device 64A having an articulating member 66A, an angled portion 68A, and a drill guide engagement portion 70A. The drill guide connection flange 64A is connected to the inner surface 28A with a mounting member 72A. The mounting member 72A is connected to the connection flange 64A with a hinge 73A, about which the articulating member 66A can pivot. The connection flange 64A is arranged such that the articulating member 66A is mounted beyond the first side surface 56A, and thus the locking tab 54A is between the articulating member 66A and the inserter passageway 34A. The articulating member 66A extends generally parallel to, but spaced apart from, the first side surface 56A. The articulating member 66A generally pivots off the mounting member 72A at the hinge 73A in response to pressure applied to the articulating member 66A by a user upon pressing or pushing the articulating member 66A toward the first side surface 56A. Extending from the articulating member 66A is the angled portion 68A, which is between the articulating member 66A and the drill guide engagement portion 70A. The drill guide engagement portion 70A extends generally parallel to the bottom surface 26A of the main body 22A. Depressing the articulation member 66A toward the side surface 56A to rotate the drill guide connection flange 64A about the hinge 73A pivots the drill guide engagement portion 70A away from the bottom surface 26A. The reload assembly 10 can be constructed of any suitable material, such as a suitable polymer to allow flexing of the locking tabs 54A and 54B, as well as the connection flanges 64A and 64B without bending or breaking.

Figure 5:
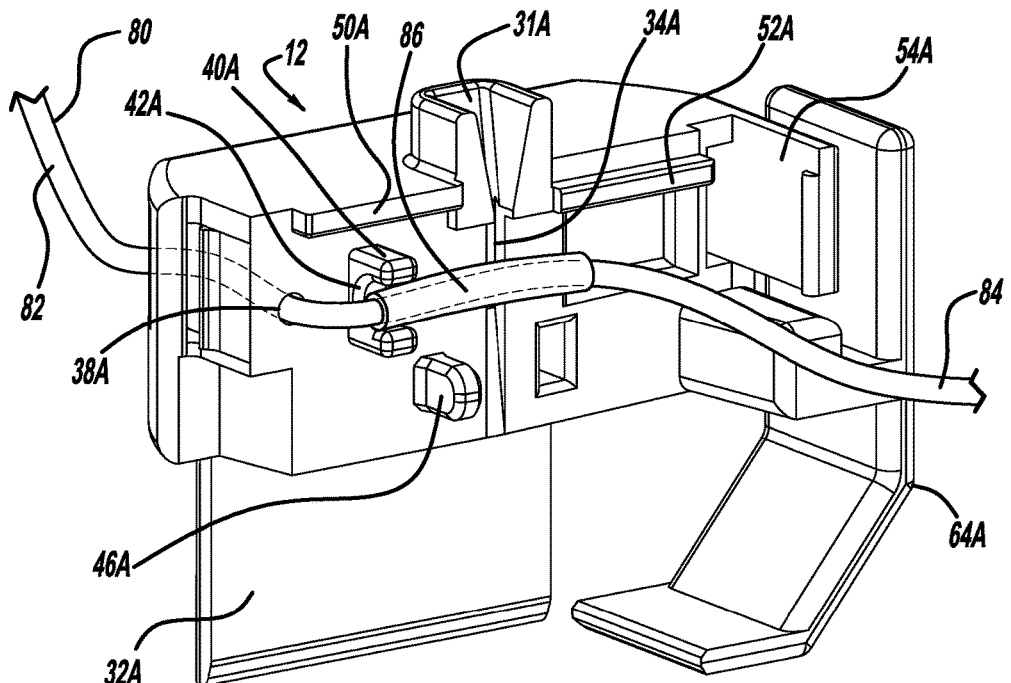
FIG. 5 is a perspective view of the first half of the reload assembly of FIG. 4 with a suture anchor in cooperation therewith.
Figure 6:
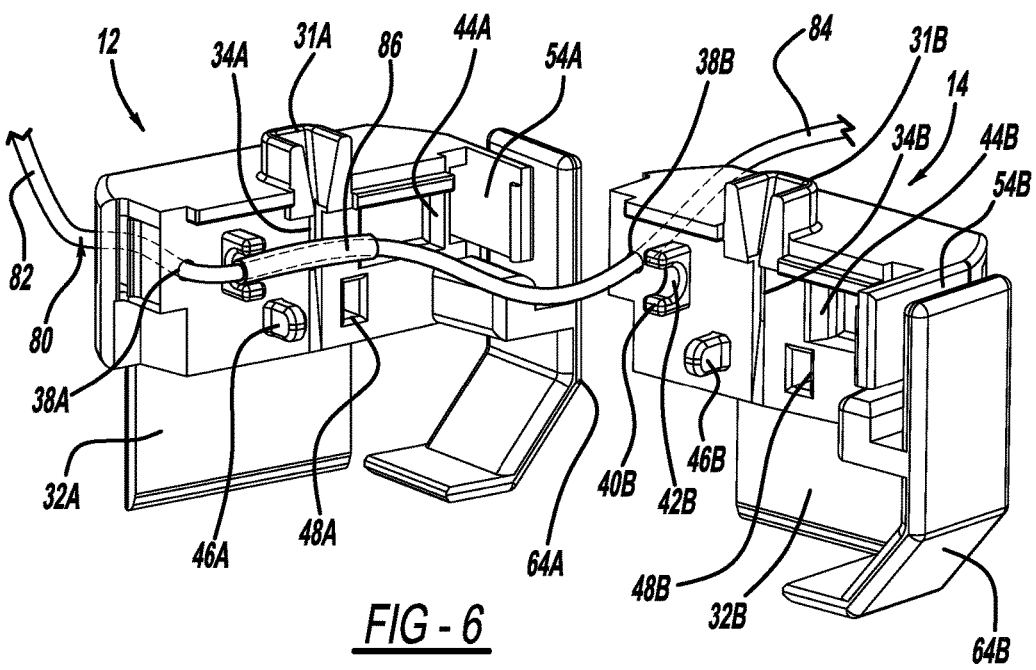
FIG. 6 is a perspective view of the first half and a second half of the reload assembly of FIG. 1 separated apart, the suture is in cooperation with both the first half and the second half.

With additional reference to FIGS. 5 and 6, a suture 80 including a first portion 82, a second portion 84, and an anchor 86 therebetween is provided. Any suitable type of suture can be used, such as a suture with a soft or hard anchor. While the examples described herein include a soft anchor, a hard anchor may be used as well. With respect to the first half 12 of the suture anchor reload assembly 10, the suture 80 is arranged such that the anchor 86 is seated against the U-shaped guide surface 42A of the suture alignment guide 40A and extends across the inserter passageway 34A, and the first portion 82 extends through the suture aperture 38A. With respect to the second half 14, the suture 80 is arranged such that the anchor 86 is seated against the U-shaped guide surface 42B of the suture alignment guide 40B and extends across the inserter passageway 34B, and the second portion 84 extends through the suture aperture 38B. The anchor 86 is arranged such that it extends generally perpendicular to the length of the inserter passageways 34A and 34B that form the inserter receptacle 18 and the longitudinal axis A.

With the suture 80 arranged as described above, the first half 12 is coupled with the second half 14 by positioning the inner surfaces 28A and 28B facing each other and pressing the first half 12 and the second half 14 together. To secure the first half 12 to the second half 14, the locking tabs 54A and 54B flex to permit the coupling flange 60A to pass over and couple to the coupling ridge 62B and the coupling flange 60B passes over and couples to the coupling ridge 62A. To assist in the coupling and alignment of the first half 12 and the second half 14, the alignment flange 46A is received by the alignment flange receptacle 48B and the alignment flange 46B is received by the alignment flange receptacle 48A. To accommodate the suture alignment guides 40A and 40B, the alignment guide 40A is received by the suture alignment guide receptacle 44B and the alignment guide 40B is received by the suture alignment guide receptacle 44A. The opposing inserter passageways 34A and 34B, and the opposing U-shaped inserter guide flanges 31A and 31B generally define the inserter receptacle 18. The suture 80 is typically mated with the suture anchor reload assembly 10, and the first half 12 is typically mated with the second half 14, prior to delivery of the suture anchor reload assembly 10 to the operating room, such as at the manufacturer.

With additional reference to FIG. 7, a drill guide and/or insertion cannula 110 for use with the suture anchor reload assembly 10 is illustrated. The suture anchor reload assembly 10 may also be used as a handheld device without being mated with a guide, inserter, or cannula. The drill guide 110 includes a handle 112 having a proximal end 114 and a distal end 116 opposite thereto. The handle 112 generally includes a first planar surface 118A and a second planar surface 118B opposite thereto. Perpendicular to the first and second planar surfaces 118A and 118B are a first gripping surface 120A and a second gripping surface 120B opposite thereto. The handle 112 may be generally rectangular, round, or otherwise shaped. The first and the second gripping surfaces 120A and 120B define a plurality of ridges 122, which facilitate grasping of the handle 112. A drill guide bore 132 extends through the handle 112 from the proximal end 114 to the distal end 116. A drill guide shaft 126 extends from the distal end 116 and terminates at a rigid or toothed end surface 127. Proximate to the end surface is a window 129 defined in the drill guide shaft 126, which can be used during operation to gauge depth of a drill or inserter for implanting the anchor 86, as further described herein. The drill guide bore 132 further extends through, and is defined by, the shaft 126.

At the proximal end 114 of the handle 112 is a first slot 124A defined in the first planar surface 118A and a second slot 124B defined in the second planar surface 118B. The first slot 124A extends perpendicular to a longitudinal axis of the drill guide 110 across the first planar surface 118A. The second slot 124B extends perpendicular to longitudinal axis B of the drill guide 110 across the second planar surface 118B.

The first planar surface 118A further includes, between the first slot 124A and the proximal end 114, a first recessed area 128A, which is recessed beneath a portion of the first planar surface 118A that is distal to the first slot 124A. Protruding from the first recessed area 128A is a first handle tab 130A, which extends across less than the entire width of the first planar surface 118A and protrudes only slightly from the first recessed area 128A such that the first handle tab 130A is not planar, and does not extend out further than, the remainder of the first planar surface 118A. Similarly, the second planar surface 118B further includes, between the first slot 124A and the proximal end 114, a second recessed area 128B, which is recessed beneath a portion of the second planar surface 118B that is distal to the second slot 124B. Protruding from the second recessed area 128B is a second handle tab 130B, which extends across less than the entire width of the second planar surface 118B and protrudes only slightly from the second recessed area 128B such that the second handle tab 130B is not planar with the remainder of the second planar surface 118B.

With additional reference to FIG. 8, cooperation between the suture anchor reload assembly 10 with the suture 80 mounted thereto and the handle 112 will now be described. The reload assembly 10 is placed over the proximal end 114 of the handle 112 such that the drill guide connection flange 64A of the first half 12 is within the first slot 124A and the drill guide connection flange 64B of the second half 14 is within the second slot 124B. More specifically, the drill guide engagement portion 70A of the first half 12 is pushed over the first handle tab 130A of the first recessed area 128A by depressing the articulation member 66A to rotate drill guide connection flange 64A about the hinge 73A and move the drill guide engagement portion 70A away from the bottom surface 26A. The drill guide engagement portion 70A is then snapped into the first slot 124A. Similarly, the drill guide engagement portion 70B of the second half 14 is snapped into the second slot 124B. Thus, it is through engagement between the drill guide engagement portions 70A and 70B, and the first slot 124A and 124B respectively that the anchor reload assembly 10 is secured to the handle 112. The alignment flange 32A of the first half 12 and the alignment flange 32B of the second half 14 are each positioned to abut and extend across opposing sides of the handle 112 that include the ridges 122 to further align and secure the reload assembly 10 at the proximal end 114 of the handle 112. The drill guide engagement portions 70A and 70B, and the alignment flanges 32A and 32B, combine to cooperate with the drill guide handle 112 to align the inserter receptacle 18 with the drill guide bore 132 and align the longitudinal axis A of the reload assembly 10 with the longitudinal axis B of the drill guide 110. Securing the reload assembly 10 to the handle 112 in this manner results in the inserter passageway 34 and the u-shaped inserter guide flange 31 being aligned with the drill guide bore 132.

Figure 9:
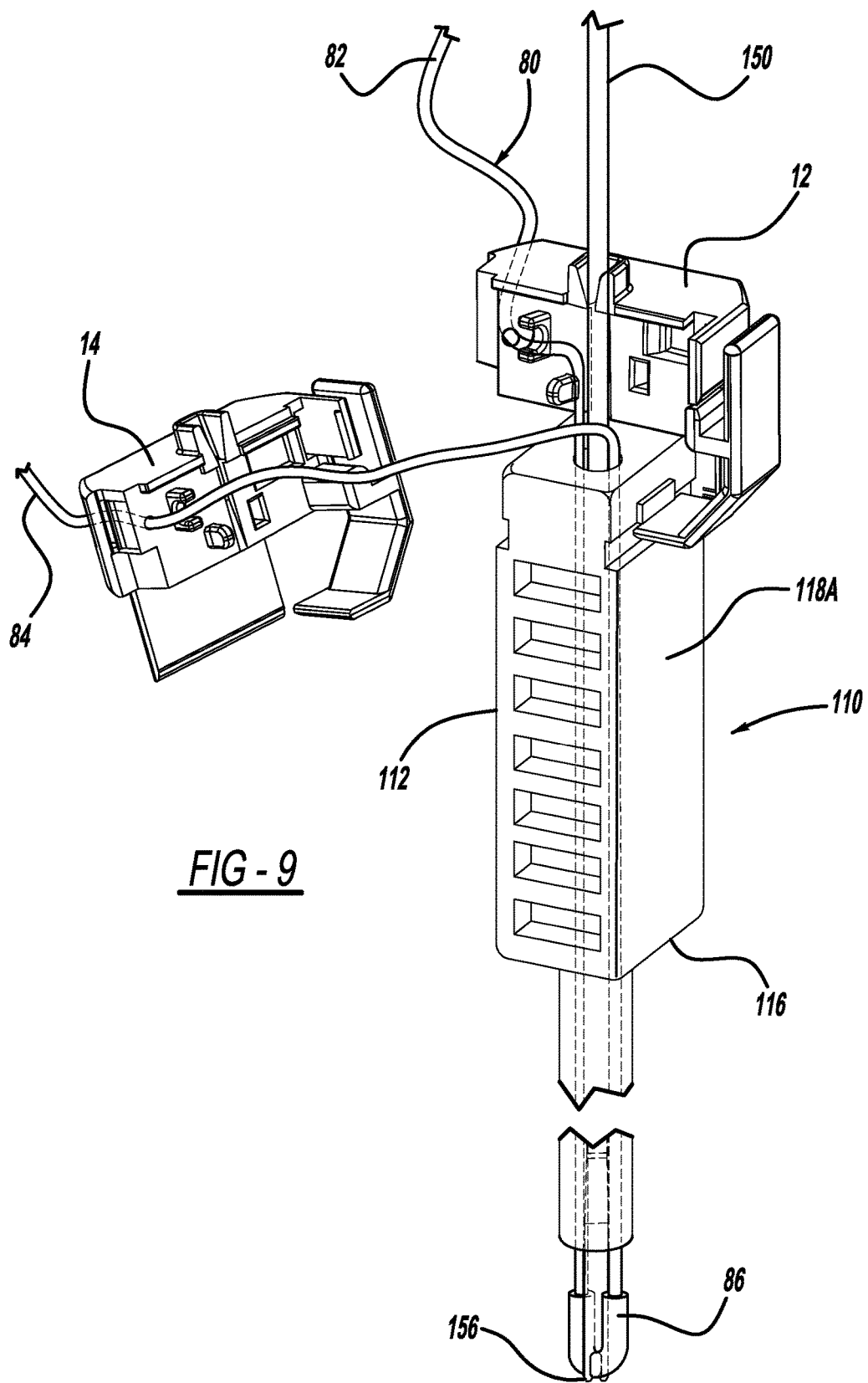
FIG. 9 is a perspective view of an inserter loaded with the suture anchor of the suture anchor reload assembly.
Figure 13:
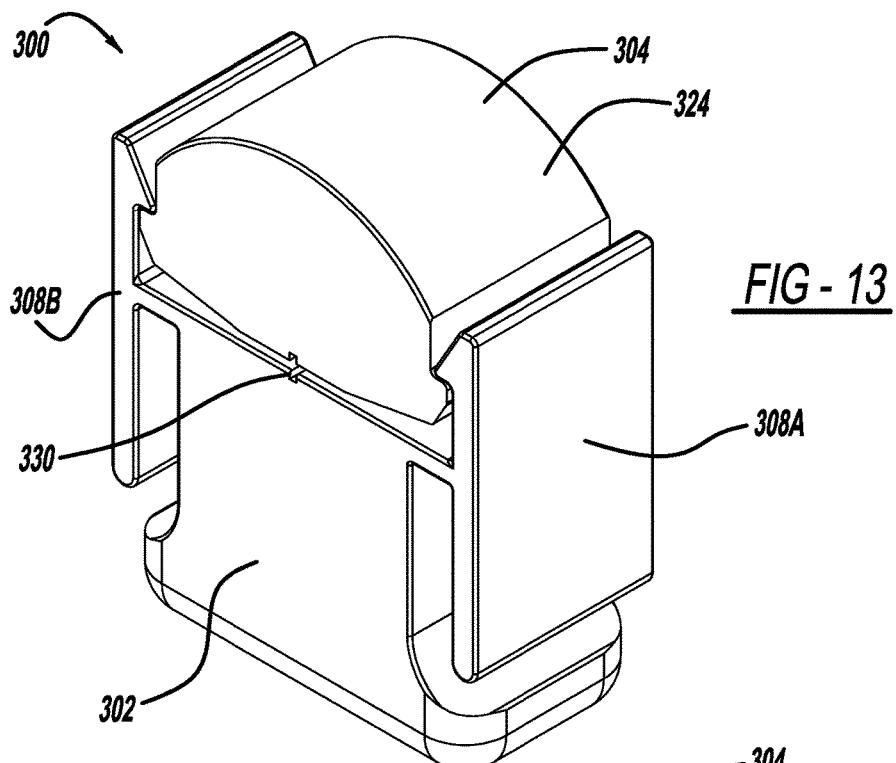
FIG. 13 is a perspective view of another suture anchor reload assembly according to the present teachings.
Figure 14:
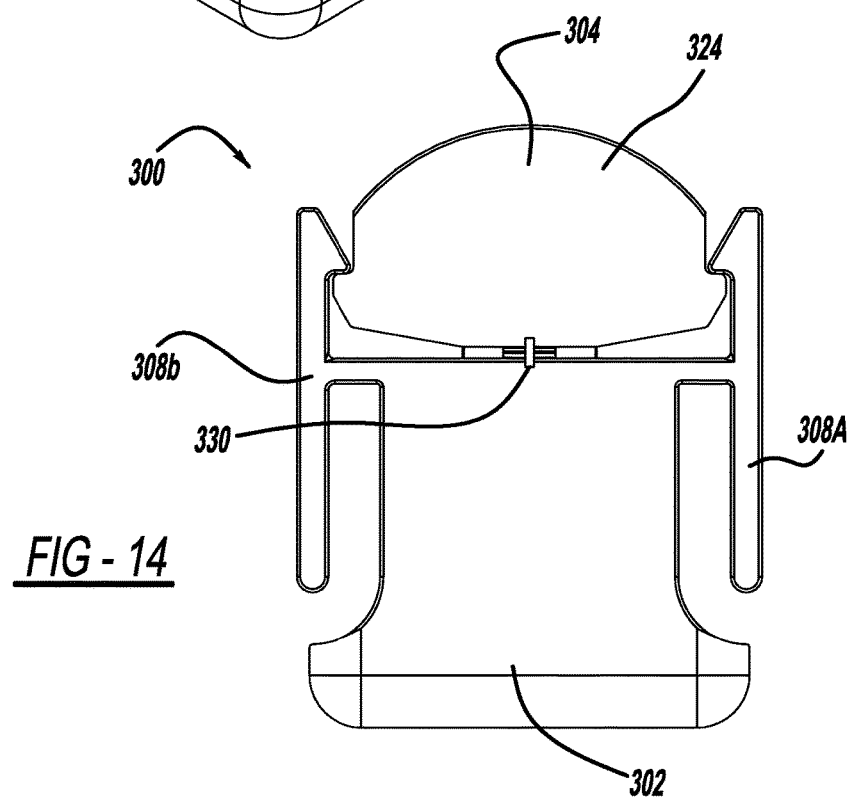
FIG. 14 is a planar view of the assembly of FIG. 13.
Figure 15:
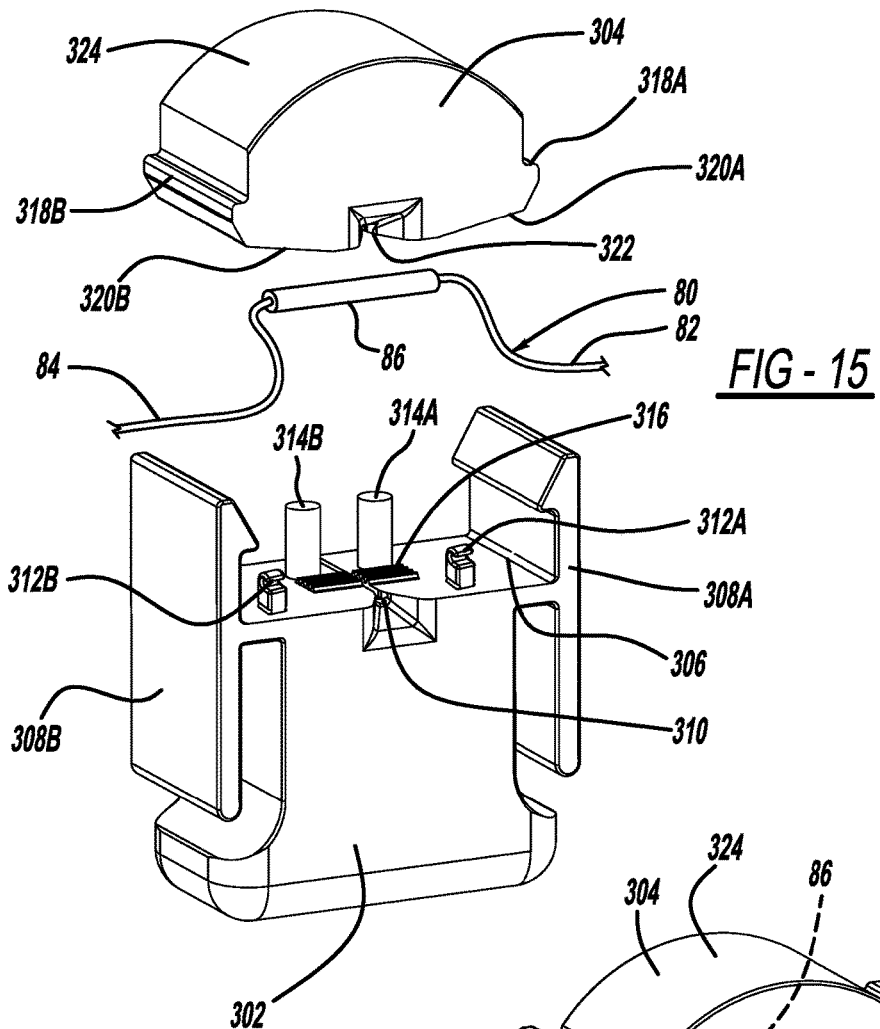
FIG. 15 is an exploded view of the assembly of FIG. 13.
Figure 16:
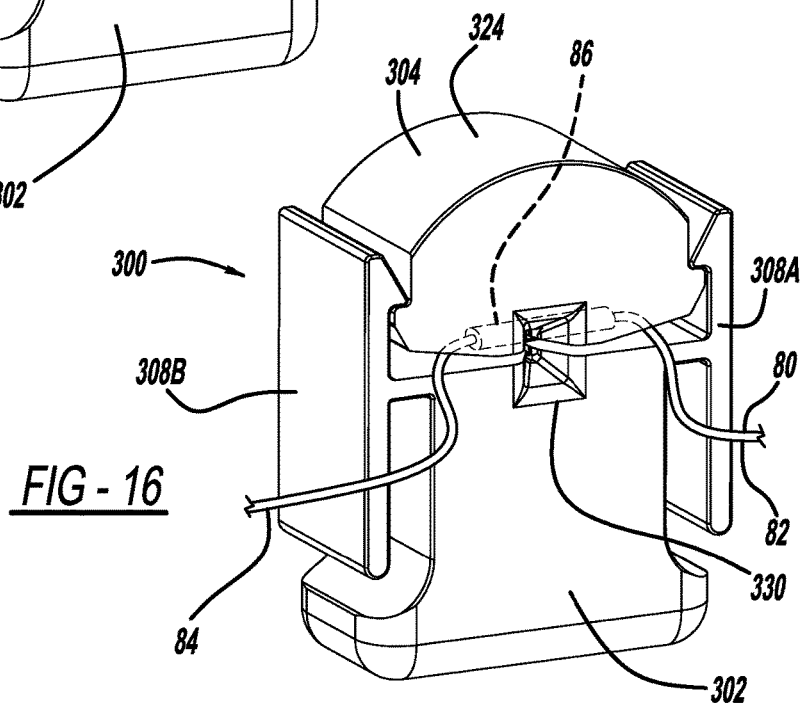
FIG. 16 is a perspective view of the assembly of FIG. 13 with a suture mounted thereto.

With additional reference to FIG. 9, loading of the suture 80 onto an inserter 150 will now be described. The inserter 150 generally includes an elongated shaft 152 with a distal end 154 defining a hook 156. The distal end 154 includes opposing planar surfaces 158A and 158B, which differs from a remainder of the shaft 152, which is generally circular in cross-section. The distal end 154 also includes a first tapered portion 160 and a second tapered portion 162, which is distal to the first tapered portion 160. An alignment or depth gauge grid 164 is at the first tapered portion 160. The grid 164 can be viewed through the window 129 during operation to assist in determining the proper insertion depth of the inserter 150. Any suitable inserter can be used, such as the JuggerKnot™ inserter by Biomet, Inc. of Warsaw, Ind. The inserter 150 can be originally provided by a vendor with a suture mounted to, which prior to being reloaded with the suture 80 using the reload assembly 10 can be used to implant the suture originally loaded thereon. Thus, the suture anchor reload assembly 10 permits the inserter 150 to be reloaded with a suture and reused, which reduces waste and material costs. The inserter 150 can also be provided by the vendor without a suture mounted thereto.

To load the inserter 150 with the suture 80, the inserter 150 is inserted into the suture anchor reload assembly 10 and into the u-shaped inserter guide flanges 31A and 31B. A shape of the guide flanges 31A and 31B corresponds to a shape of the distal end 154 of the inserter 150, and thus can combine to form a generally rectangular shape, to orientate the hook 156 such that it engages and receives the anchor 86 as the distal end 154 is pushed into and along the inserter receptacle 18. The guide flanges 31A and 31B are thus keyed, such as with the opposing planar surfaces 158A and 158B to align the hook 156 so that the anchor 86 is arranged between two opposing teeth 157A and 157B of the hook 156 and so that the hook 156 grasps the anchor 86. The inserter 150 is pushed through the drill guide bore 132 such that the hook 156 extends from the shaft 126 with the suture 80 loaded thereon for implantation, as illustrated in FIG. 9. As the inserter 150 is pushed through the inserter receptacle 18, upon contacting the angled surfaces 36A and 36B, which progressively narrow the inserter receptacle 18, the first half 12 and the second half 14 of the reload assembly 10 are urged apart until they eventually separate automatically, as illustrated in FIG. 9, so that they are out of the way during implantation of the suture 80. The first portion 82 and the second portion 84 remain seated within the suture apertures 38A and 38B respectively to prevent the first and the second halves 12/14 from, for example, dropping to the operating room floor. The suture 80 can be used in any conventional manner, such as to secure two area of biological matter together, such as two tissue areas, two bony areas, or a tissue area to a bony area.

An exemplary method of operation for the suture anchor reload assembly 10 will now be described. The drill guide 110 can be driven into bone or tissue by impaction or any other suitable manner. A drill can be inserted through the drill guide bore 132 to drill a hole in the bone or tissue. An inserter, such as the inserter 150, preloaded with a suture including an anchor, such as the suture 80, can be inserted through the drill guide bore 132 for implantation. To implant another suture anchor, the same inserter 150 can be used. Specifically, the reload assembly 10 with the suture 80 mounted thereto can be attached to the handle 112 of the drill guide 110, as described above, and the drill guide 110 can be moved to a different implant site. The inserter 150 may then be driven through the inserter receptacle 18 as described above to capture the suture 80 for insertion. In a similar manner, the inserter 150 can be used to implant any suitable number of additional suture anchors.

With additional reference to FIGS. 10-12, another suture anchor reload assembly according to the present teachings is illustrated at reference numeral 200. The assembly 200 can be handheld as the illustrated example is, or can be configured for attachment to a suitable alignment guide. The assembly 200 generally includes a base member 202, a first reload cartridge 204, a second reload cartridge 206, an end reload cartridge 208, and first, second, and third retention clips 210A-210C. While two reload cartridges 204 and 206 are illustrated and described, a single reload cartridge can be provided, as well as any suitable number in addition to two. The assembly 200 can accommodate a plurality of sutures 80, which may be provided separately or coupled to one another.

The base member 202 generally includes a body portion 212 with a first flange 214A and a second flange 214B on opposite sides thereof forming a coupling device. A suture housing 216 extends from a front surface 220 of the body portion 212 and defines a suture bore 218, which extends through both the suture housing 216 and the body portion 212. The front surface 220 is opposite to a rear surface 222. A pair of angled mating surfaces 224A and 224B are at an undersurface of the body portion 212 and both extend from opposite sides of an inserter recess 226, which extends from the front surface 220 to the rear surface 222. A gripping tab 228 also extends from the body portion 212. The gripping tab 228 can be sized and shaped to accommodate a user's thumb, to permit the user to easily maneuver the suture anchor reload assembly 200.

The first reload cartridge 204 generally includes a cartridge body 230 with a first cartridge flange 232A and a second cartridge flange 232B extending therefrom, which generally form a coupling device. A suture housing 234 extends from the body 230 and defines a suture bore 236, which extends through the body 230. The housing 234 includes angled outer surfaces 238A and 238B, each of which extend from inserter recess 240.

At a side of the cartridge body 230 opposite to the angled outer surfaces 238A and 238B is a suture retention portion 242. An inserter recess 244 is defined by the body 230 and extends across the suture retention portion 242. The suture retention portion 242 includes a pair of suture holding members or suture alignment guides 246A and 246B on opposite sides of the inserter recess 244, each of which include hooked portions 247A and 247B configured to receive and secure the suture 80 such that the suture 80 extends across the inserter recess 244. To further assist with alignment of the suture 80 as described herein, first and second knobs 248A and 248B are arranged on opposite sides of the inserter recess 244 between the suture alignment guides 246A and 246B and the inserter recess 244. Extending in a general vertical direction from the suture retention portion 242 are a first retention flange 250A including a first tab 252A and a second retention flange 250B including a second tab 252B, which generally form a coupling device. The first and the second tabs 252A and 252B face each other and are on an inside of the first and second retention flanges 250A and 250B respectively. On an outside of the first retention flange 250A is a recessed outer surface 254A and on an outside of the second retention flange 250B is a recessed outer surface 254B. As further described herein, recessed outer surfaces 254A and 254B are configured to cooperate with the first retention clip 210A.

The second reload cartridge 206 is substantially similar to the first reload cartridge 204 and thus the description of the first reload cartridge 204 also applies to the second reload cartridge 206. Features of the second reload cartridge 206 that are similar to the first reload cartridge 204 are designated with like reference numbers including the prime (') symbol.

The end reload cartridge 208 includes a body 256 with a generally planar undersurface 258. Opposite to the body 256 is suture retention portion 242", which is substantially similar to both the suture retention portion 242 of the first reload cartridge 204 and the suture retention portion 242' of the second reload cartridge 206. Features of the suture retention portion 242" that are the same as or substantially similar to the features of the suture retention portions 242 and 242' are designated with like reference numbers including the double prime (") symbol.

The first retention clip 210A, the second retention clip 210B, and the third retention clip 210C are substantially similar to one another. The following description of the first retention clip 210A thus equally applies to the second retention clip 210B and the third retention clip 210C as well. The first retention clip 210A generally includes an elongated portion 260 with a first clip flange 262A and a second clip flange 262B at opposite ends thereof. At a midpoint of the elongated portion 260 is a first recess 264A and a second recess 264B. The first and the second recesses 264A and 264B each have a generally semi-circular shape and are arranged opposite to one another. The recesses 264A and 264B are generally sized and shaped to accommodate the suture housings 216, 234, and 234'.

Arrangement of the sutures 80 within the assembly 200 and cooperation of the different components of the assembly 200 will now be described. The base member 202 is coupled to the first reload cartridge 204 through cooperation between the first and second retention flanges 250A and 250B of the cartridge 204 and the first and second flanges 214A and 214B of the base member 202 respectively. The retention flanges 250A and 250B are biased outward such that they do not hook onto the first and the second flanges 214A and 214B respectively until retention clip 210A is coupled to the first and the second retention flanges 250A and 250B. This coupling is performed by pressing the first clip flange 262A onto the recessed outer surface 254A and pressing the second clip flange 262B onto the second recessed surface 254B to flex and draw the first and second retention flanges 250A and 250B together such that the first tab 252A engages the first flange 214A of the base member 202 and the second tab 252B engages the second flange 214B of the base member 202.

Prior to coupling the first reload cartridge 204 to the base member 202, the suture 80 is placed into cooperation with the suture alignment guides 246A and 246B such that the anchor 86 extends across or between the suture alignment guides 246A and 246B. The anchor 86 thus also extends across the inserter recess 244 generally perpendicular thereto. From the suture retention portion 242 the first and second suture portions 82 and 84 extend to the rear surface 222 and through the suture bore 218 from the rear surface 222. After the first reload cartridge 204 is coupled to the base member 202, the anchor 86 is sandwiched between the inserter recess 244 of the first reload cartridge 204 and the inserter recess 226 of the base member 202. The inserter recess 226/244 combine to form inserter receptacle 266 (FIG. 12). The angled mating surfaces 224A and 224B of the base member 202 provide a clearance at the suture retention portion 242 for the first and the second portions 82 and 84 of the suture. The angled mating surfaces 224A and 224B define receptacles (not shown) to accommodate the suture alignment guides 246A/246B and the knobs 248A/248B of the suture retention portion 242.

Another suture 80 is mounted to the suture retention portion 242' of the second reload cartridge 206, and yet another suture 80 is mounted to the suture retention portion 242" in the same manner as described above. The sutures 80 can be separate individual sutures or linked end to end. The second reload cartridge 206 is connected to the first reload cartridge 204 by clamping the first and second retention flanges 250A' and 250B' onto the first and second cartridge flanges 232A and 232B respectively with the second retention clip 210B, similar to how the retention flanges 250A/250B are clamped onto the first and second flanges 214A/214B described above. The end reload cartridge 208 is connected to the second reload cartridge 206 by clamping the first and second retention flanges 250A" and 250B" onto the first and second cartridge flanges 232A' and 232B' respectively with the clip 210C.

Use of the suture anchor reload assembly 200 to load the sutures 80 onto a suitable inserter, such as the inserter 150, will now be described, particularly with reference to the assembled view of FIG. 12. The suture anchor reload assembly 200 can be operated as a hand held device by a person grasping the gripping tab 228, and need not be mated with a drill guide 110 or other device. While grasping the gripping tab 228 with one hand, for example, a user of the assembly 200 can push the inserter 150 into the inserter receptacle 268 as defined by the cooperation of the inserter recess 244" of the end reload cartridge 208 and the inserter recess 240' of the second reload cartridge 206. The inserter receptacle 268 is keyed to orient the teeth 157A and 157B on opposite sides of the anchor 86 of the suture 80 so that the hook 156 of the inserter 150 hooks onto the anchor 86. As the inserter 150 is further pushed into and through the inserter receptacle 268, the inserter 150 contacts the third retention clip 210C to dislodge the third retention clip 210C from engagement with the end reload cartridge 208. This contact releases the first and the second retention flanges 250A" and 250B" from cooperation with the cartridge flanges 232A' and 232B' respectively. As a result, the end reload cartridge 208 detaches from the second reload cartridge 206. Using the inserter 150, the suture 80 can then be implanted as desired, such as in tissue and/or bone. Similarly, the inserter 150 can be inserted into, with reference to FIG. 12, inserter receptacles 266 and 270 to load additional sutures 80 onto the same inserter 150, thus reducing waste and manufacturing costs.

With additional reference to FIGS. 13-16, another suture anchor reload assembly according to the present teachings is illustrated at reference numeral 300. The assembly 300 can be handheld as the illustrated example is, or can be configured for attachment to a suitable alignment guide. The assembly 300 generally includes a body 302 and a head 304 releasably secured thereto. The body 302 generally includes a suture retention portion 306 (FIG. 15) between a first coupling flange 308A and a second coupling flange 308B. The suture retention portion 306 defines a body inserter recess 310 therein, a pair of suture alignment guides or anchor holders 312A and 312B, and a pair of suture guide knobs 314A and 314B. The suture alignment guides 312A and 312B can be configured and arranged similar to the suture alignment guides 246A and 246B of the first reload cartridge 204, for example, and thus the description of the suture alignment guides 246A and 246B also describes the suture alignment guides 312A and 312B. The guide knobs 314A and 314B can be configured and arranged similar to the guide knobs 248A and 248B of the first reload cartridge 204, for example, and thus the description of the guide knobs 248A and 248B also describes the guide knobs 314A and 314B. The suture retention portion 306 can further include a roughened surface 316 aligned with the suture alignment guides 312A and 312B on opposite sides of the body inserter recess 310 to facilitate retention of the anchor 86 across the inserter recess 310 as a result of the anchor 86 being compressed thereon when the head 304 is connected to the body 302 as described herein.

The head 304 generally includes first and second opposing coupling ridges 318A and 318B, which together with the first and the second coupling flanges 308A and 308B form a coupling device. First and second suture engagement surfaces 320A and 320B each extend along an undersurface of the head 304 at opposite sides of a head inserter recess 322. Opposite to the first and second suture engagement surfaces 320A and 320B is a semi-circular outer surface 324, which extends from about the first coupling ridge 318A to about the second coupling ridge 318B.

The suture 80 is arranged on the suture retention portion 306 such that the anchor 86 extends across the body inserter recess 310 and is anchored at the suture alignment guides 246A and 246B. With the suture 80 in position, the head 304 is locked onto the suture retention portion 306 through interaction between the first coupling ridge 318A and the first coupling flange 308A, as well as between the second coupling ridge 318B and the second coupling flange 308B. The anchor 86 will thus be sandwiched between the body inserter recess 310 and the head inserter recess 322, which define an inserter receptacle 330. The first and the second portions 82 and 84 of the suture 84 are arranged to extend from the suture retention portion 306. The angled first and second suture engagement surfaces 320A and 320B provide clearance between the head 304 and the suture retention portion for the suture 84.

During use, the suture anchor assembly 300 is grasped by the user at the body 302 and a suitable inserter, such as the inserter 150, is inserted into the inserter receptacle 330, which expands outward at the body inserter recess 310 to facilitate insertion of the inserter 150 therein. The inserter receptacle 330 is keyed such that the teeth 157A and 157B are oriented on opposite sides of the anchor 86 so that the anchor 86 is received within the hook 156 of the inserter 150. As the inserter 150 is pushed within the inserter receptacle 330 it causes the head 304 to separate from the body 302. Simultaneously, the hook 156 of the inserter 150 engages the anchor 86 and pushes it through the guide knobs 314A and 314B to fold the anchor 86 and prepare it for implantation at a suitable site.

Figure 17:
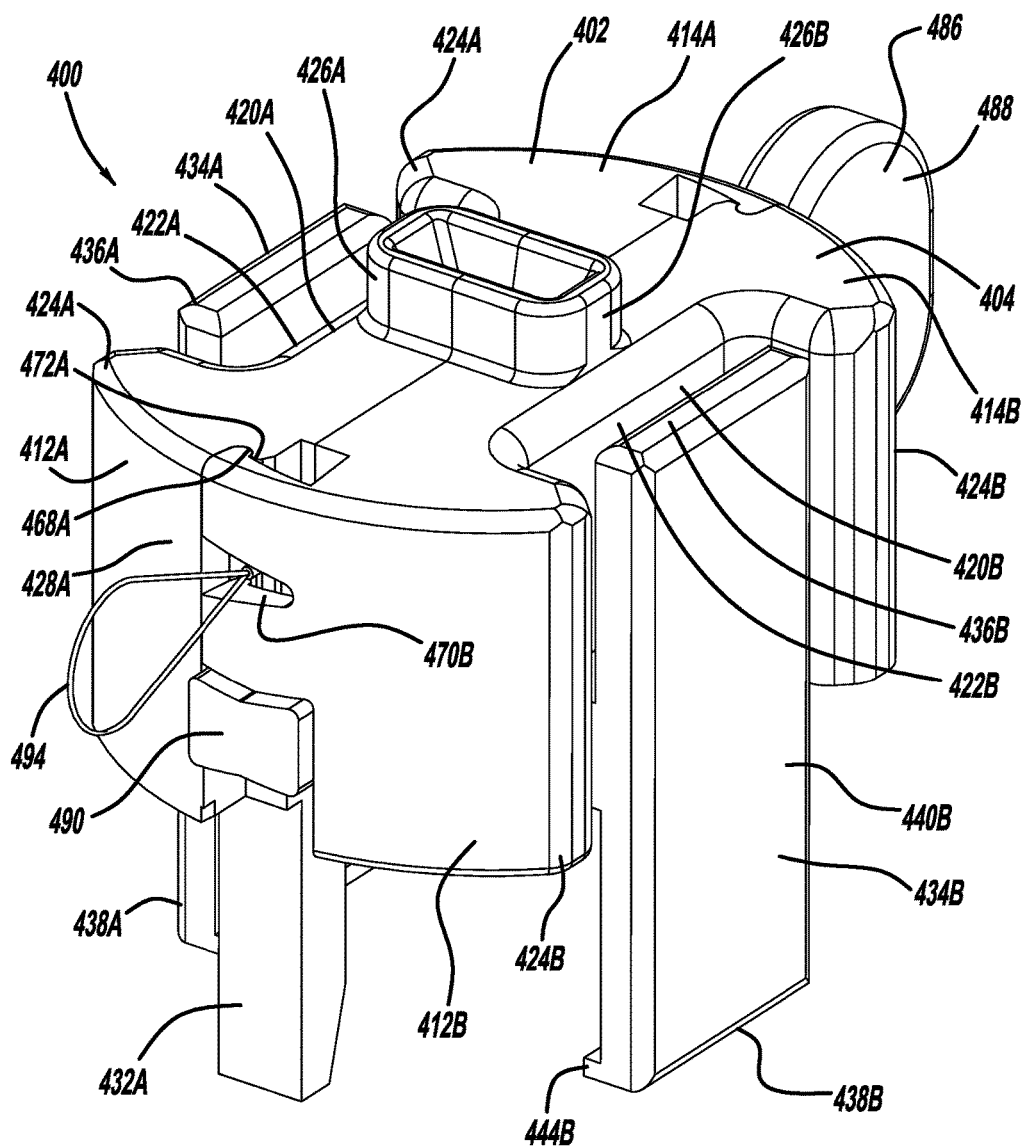
FIG. 17 is a perspective view of another suture anchor reload assembly according to the present teachings.
Figure 18:
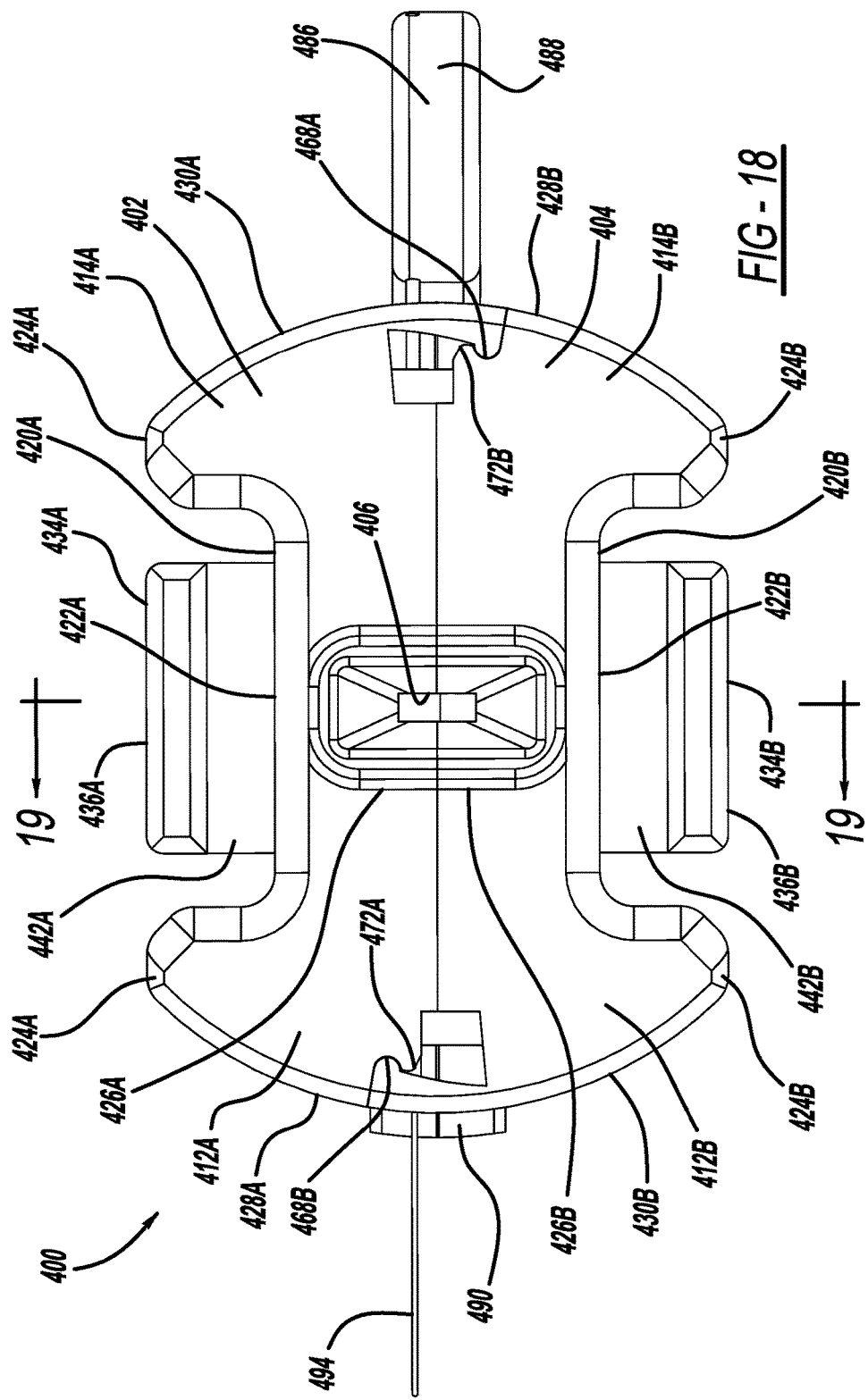
FIG. 18 is a top planar view of the suture anchor reload assembly of FIG. 17.
Figure 19:
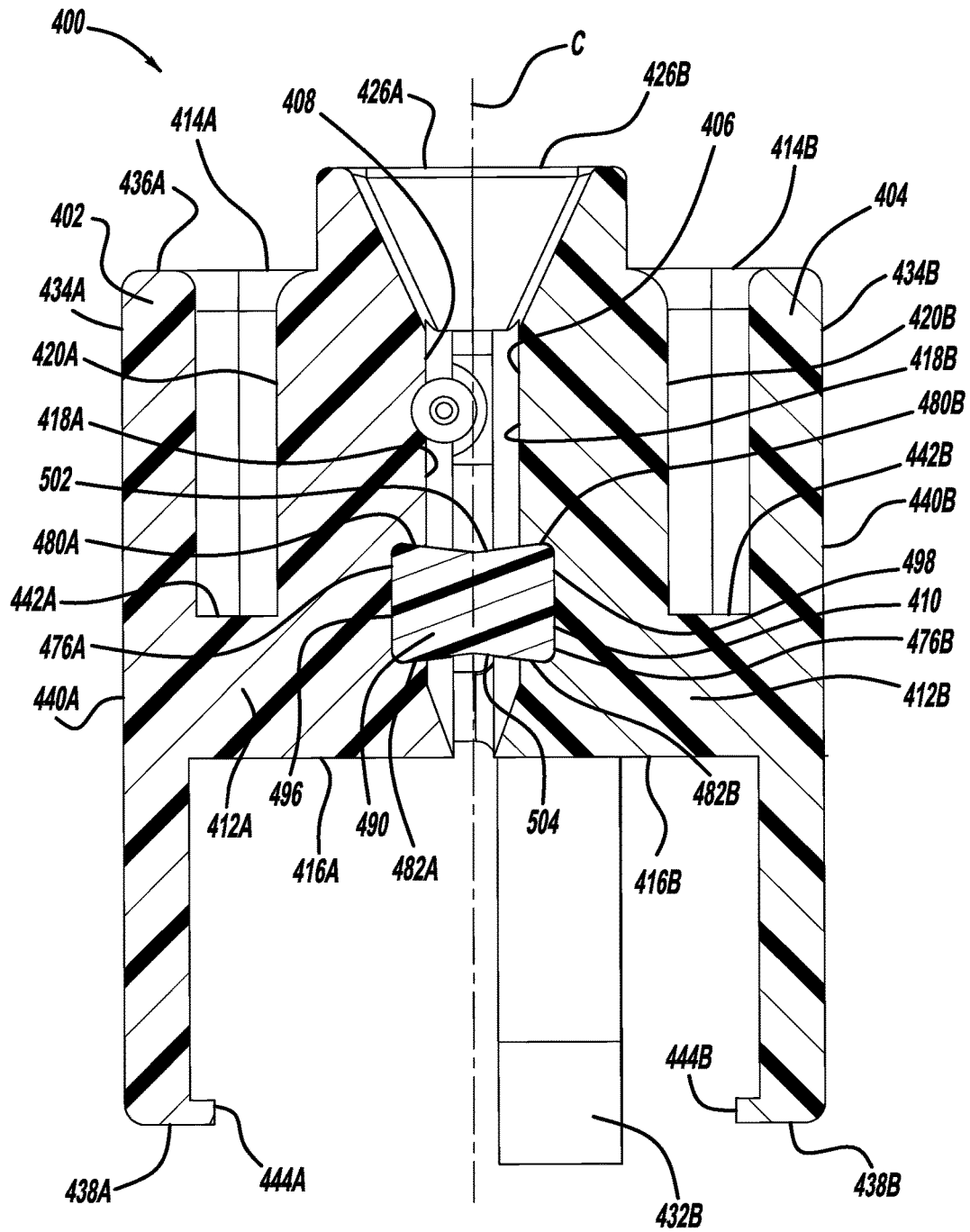
FIG. 19 is cross-sectional view taken along line 19-19 of FIG. 18.

With reference to FIGS. 17-19, another anchor reload assembly is generally illustrated at reference numeral 400. The reload assembly 400 generally includes a first portion or half 402 and a second portion or half 404, which can be substantially similar to one another, or identical as illustrated to facilitate manufacturing and reduce costs, for example. The first and the second halves 402 and 404 connect together to define, for example, an inserter receptacle 406 (FIGS. 18 and 19), a suture anchor cavity 408 (FIG. 19), and a retention pin cavity 410 (FIG. 19). The suture anchor reload assembly 400 can also be configured such that the first and the second halves 402 and 404 separate along a line perpendicular to a longitudinal axis of suture anchor cavity 408, as described further herein. The anchor reload assembly 400 can also be monolithic.

With continued reference to FIGS. 17-19 and additional reference to FIG. 20, features of the first half 402 will be described. Because the first half 402 and the second half 404 are at least substantially identical, the description of the first half 402 also applies to the second half 404. To distinguish between the first half 402 and the second half 404, features of the first half 402 are designated with the letter "A" and features of the second half 404 are designated with the letter "B."

The first half 402 generally includes a main body 412A having a top surface 414A, a bottom surface 416A, an inner surface 418A, and an outer surface 420A. The top surface 414A and the bottom surface 416A are generally planar and extend parallel to one another. The top surface 414A is opposite to the bottom surface 416A and the inner surface 418A is opposite to the outer surface 420A. The inner surface 418A of the first half 402 and the inner surface 418B of the second half 404 generally define the suture anchor cavity 408. The outer surface 420A includes a generally planar portion 422A between two winged or extending portions 424A, which the planar portion 422A is recessed between. The inner surface 418A is generally concave with respect to the planar portion 422A, thereby defining the suture anchor cavity 408 as generally tapered outward in opposite directions from a longitudinal axis C (FIG. 19) of the suture anchor reload assembly 400.

Extending from the top surface 414A is an inserter guide flange 426A, which is generally U-shaped. Extending from the bottom surface 416A proximate to a first side surface 428A of the first half 402, which is opposite to a second side surface 430A, is a flange 432A. The flange 432A facilitates alignment of the reload assembly 400 with a cannula or guide, such as a drill guide. The flange 432A can also include a coupling feature, such as at a distal end thereof, to couple the reload assembly 400 with the cannula or guide.

The first half 402 further includes a flexible drill guide connection flange or coupling device 434A extending from the planar portion 422A of the outer surface 420A. The connection flange 434A includes an articulating end 436A, a drill guide engagement end 438A, an elongated planar portion 440A extending between the articulating end 436A and the drill guide engagement end 438A, and a connecting hinge 442A extending between the elongated planar portion 440A and the outer surface 420A about equidistant between the articulating end 436A and the drill guide engagement end 438A. At the drill guide engagement end 438A is a drill guide engagement portion 444A that extends in the same direction as the connecting hinge 442A.

The articulating end 436A generally pivots at the hinge 442A in response to pressure applied to the articulating end 436A by a user upon pressing or pushing the articulating end 436A toward the outer surface 420A. The drill guide engagement portion 444A extends generally parallel to the bottom surface 416A of the main body 412A. Depressing the articulating end 436A toward the outer surface 420A to rotate the drill guide connection flange 434A about the hinge 442A pivots the drill guide engagement portion 444A away from the bottom surface 416A. The reload assembly 400 can be constructed of any suitable material, such as a suitable polymer to allow flexing of the connection flanges 434A and 434B without bending or breaking.

The inner surface 418A defines an inserter passageway or slot 450A, which extends from the U-shaped inserter guide flange 426A to the bottom surface 416A. The inserter passageway 450A is substantially the same as the inserter passageway 34A and thus the description of the inserter passageway 34A also describes the inserter passageway 450A.

A suture holding member or suture alignment guide 452A, which includes a flange, extends out from the inner surface 418A and defines a generally U-shaped guide surface 454A. The suture alignment guide 452A is between the first side surface 428A and the inserter passageway 450A. Aligned with the suture alignment guide 452A, and at a side of the inserter passageway 450A opposite to the suture alignment guide 452A, is a suture alignment guide receptacle 456A. The receptacle 456A is defined by, and recessed within, the inner surface 418A to accommodate the suture alignment guide 452B of the second half 404 of the suture anchor reload assembly 400.

An alignment flange 458A for aligning the first half 402 with the second half 404 extends out from the inner surface 418A on the same side of the inserter passageway 450A as the suture alignment guide 452A. The alignment flange 458A is closer to the bottom surface 416A than the suture alignment guide 452A is, and is nearly adjacent to the bottom surface 416A. Aligned with the alignment flange 458A on an opposite side of the inserter passageway 450A is an alignment flange receptacle 460A, which is recessed within and defined by the inner surface 418A. The alignment flange receptacle 460A is sized and shaped to receive the alignment flange 458B of the second half 404 when the first half 402 is connected to the second half 404, as further described herein.

Extending from the inner surface 418A proximate to the top surface 414A are a first spacing tab 462A and a second spacing tab 464A. The first spacing tab 462A and the second spacing tab 464A are arranged on opposite sides of the inserter passageway 450A. The first spacing tab 462A and the second spacing tab 464A extend from the inner surface 418A to a distance less than either the suture alignment guide 452A or the alignment flange 458A. When the first half 402 and the second half 404 of the reload assembly 400 are coupled together, the first spacing tab 462A and the second spacing tab 464A extend to a distance sufficient to space the inner surface 418A from the inner surface 418B and define the suture anchor cavity 408 therebetween.

A flexible locking tab or coupling device 466A extends from the main body 412A generally at second side surface 430A of the main body 412A. The locking tab 466A extends in a direction generally perpendicular to the inner surface 418A. At an end of the locking tab 466A opposite to the inner surface 418A is a coupling flange 468A. The coupling flange 468A defines a suture aperture 470A, which interrupts the coupling flange 468A and is generally aligned with the suture alignment guide 452A.

At the first side surface 428A is a locking tab coupling ridge 472A. The locking tab coupling flange 468A is configured to mate with the coupling ridge 472B of the second half 404 and the coupling flange 468B is configured to mate with the coupling ridge 472A to secure the first half 402 of the reload assembly to the second half 404 of the reload assembly (FIG. 18). When the first and the second halves 402 and 404 are coupled, the suture aperture 470B of the locking tab 466B is aligned with the suture aperture 470A and the suture alignment guide 452A to accommodate a suture and suture anchor, as further described herein.

Figure 20:
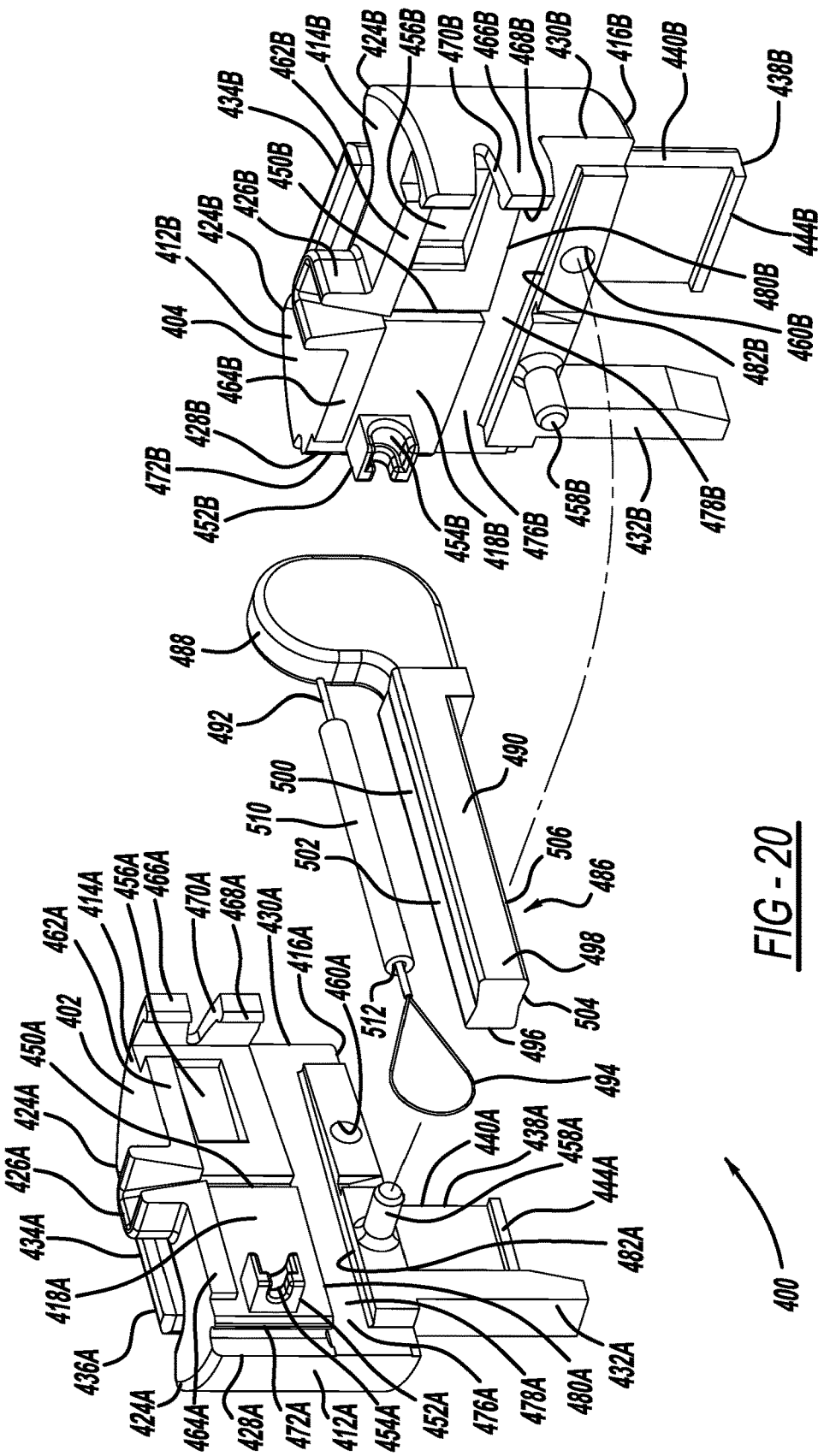
FIG. 20 is a perspective view of a first portion, a second portion, and a retention pin of the suture anchor reload assembly of FIG. 17.

With particular reference to FIGS. 19 and 20, the inner surface 418A further defines a first side 476A of the retention pin cavity 410 between the suture alignment guide 452A and the alignment flange 458A. The first side 476A includes a recessed surface 478A of the inner surface 418A extending between the first and the second side surfaces 428A and 428B of the first half 402. The inner surface 418A defines an upper slot 480A and a lower slot 482A on opposite sides of the recessed surface 478A. The upper slot 480A is proximate to the top surface 414A and the lower slot 482A is proximate to the bottom surface 416A. The upper slot 480A and the lower slot 482A each extend between the first and the second side surfaces 428A and 428B.

With reference to FIG. 20, a retention pin is illustrated at reference number 486. The retention pin 486 generally includes a handle 488, an elongated key portion 490, and a suture capture member, which is illustrated as a suture capture rod 492 extending from the handle 488 and terminating in a loop 494. The elongated key portion 490 also extends from the handle 488 and extends generally parallel to the rod 492. The key portion 490 is generally shaped and sized to mate with both the first side 476A and the second side 476B of the retention pin cavity 410. The key portion 490 includes a first planar portion 496 and a second planar portion 498, each of which extend generally parallel to one another from the handle 488.

Extending between the first and the second planar portions 496 and 498 at an upper surface 500 of the elongated key portion 490 is an upper tapered surface 502. A lower tapered surface 504 extends between the first and the second planar portions 496 and 498 at a lower surface 506 of the elongated key portion 490. The upper tapered surface 502 is sized and shaped to couple with the upper slots 480A and 480B, and the lower tapered surface 504 is sized and shaped to couple with the lower slots 482A and 482B to couple the first and the second halves 402 and 404 of the suture anchor reload assembly 400 together. The suture anchor reload assembly 400 can be provided by the manufacturer with the first and the second halves 402 and 404 coupled together with the retention pin 486. The retention pin 486 prevents premature decoupling of the first and the second halves 402 and 404.

The suture capture rod 492 is positioned such that the rod 492 extends through both the suture apertures 470A and 470B, through the suture alignment guides 452A and 452B, and across the inserter receptacle 406. The loop 494 extends out of the suture anchor reload assembly 400 through the suture aperture 470B. A suture anchor 510 is seated on the suture capture rod 492 such that the rod 492 extends through an interior 512 of the anchor 510. The anchor 510 is seated within each of the alignment guides 452A and 452B, and across the inserter receptacle 406. Any of the other suture anchor reload assemblies set forth herein can be modified to include the retention pin 486.

Figure 21:
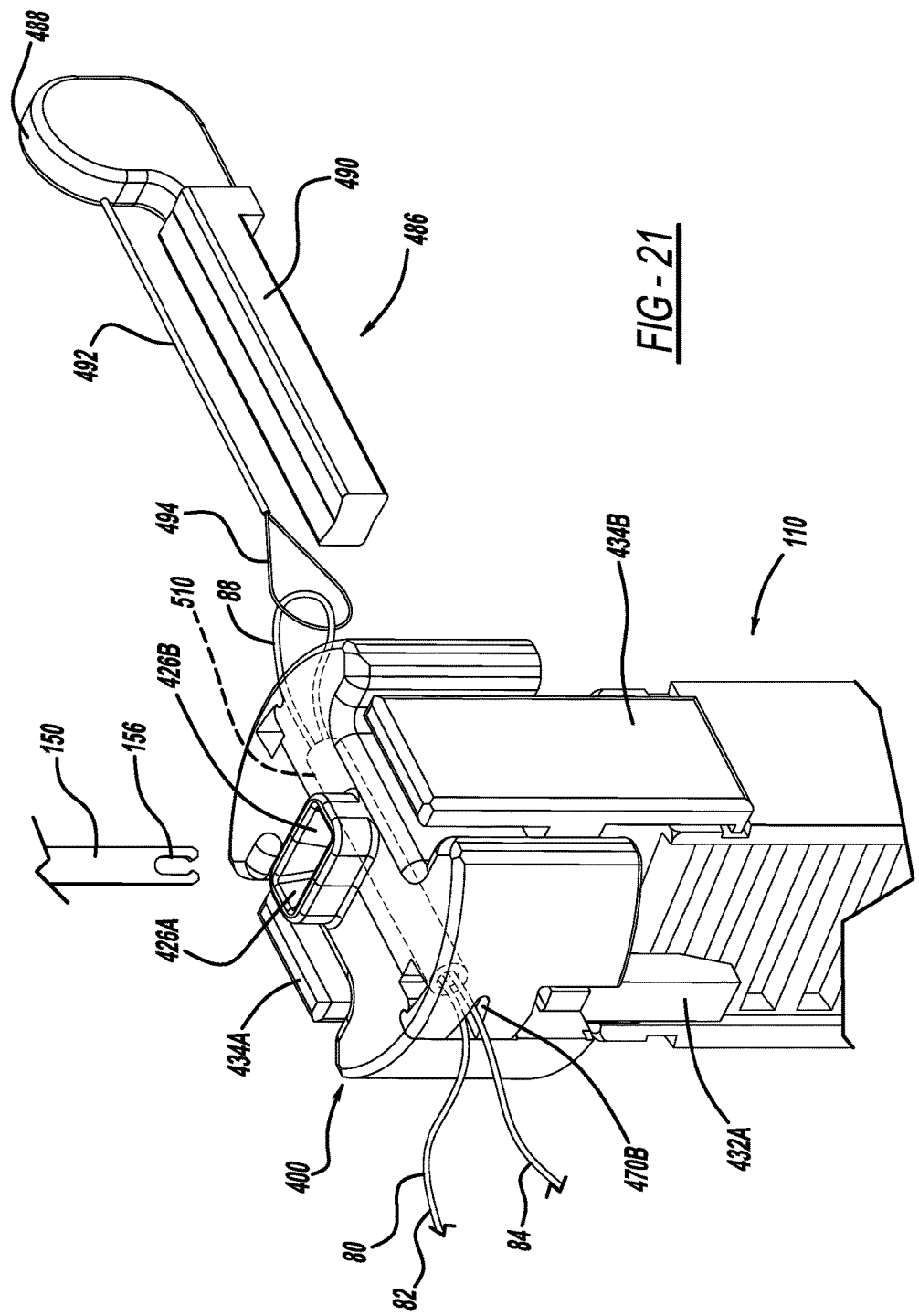
FIG. 21 illustrates use of the suture anchor reload assembly of FIG. 17 to load a suture on a soft anchor.

To load the anchor 510 on a suture, such as the suture 80 of FIG. 6, the suture 80 is first inserted through the loop 494 such that a loop portion 88 of the suture 80 is connected to the loop 494. The handle 488 is then grasped and the retention pin 486 is withdrawn from within the anchor reload assembly 400, as illustrated in FIG. 21 for example. As the retention pin 486 is withdrawn, the suture 80 is pulled into, and partially through, the interior 512 of the anchor 510. Because the suture 80 is looped through the loop 494, both the first and the second portions 82 and 84 of the suture 80 are initially on the same side of the anchor 510 as it is pulled through the interior 512 and two parallel portions of the suture 80 are initially pulled through the interior 512. Subsequently, one of either the first portion 82 or the second portion 84 is pulled through the anchor 510 so that the anchor 510 is between the first portion 82 and the second portion 84. The suture 80 can be positioned such that the anchor 510 is on any desired portion of the suture 80, such as at a mid-portion of the suture. With the anchor 510 loaded on the suture 80, the anchor 510 can be implanted in any suitable manner, such as by using the inserter 150 as described above in connection with FIGS. 8 and 9. Multiple sutures can be inserted through the loop 494 in order to attach multiple sutures to the anchor 510.

The suture 80 can be loaded onto the anchor 510 intra-operatively, which would allow a surgeon to pass the suture 80 through tissue before loading the anchor 510 on the suture. Also, multiple anchors 510 can be attached to a single suture 80. For example, after a first anchor 510 is attached to the suture 80 as described above, a second anchor 510 of another suture anchor reload assembly 400 can be loaded on the suture 80 in the same manner as described above. Instead of the first and second anchors 510 being in separate anchor reload assemblies 400 as described above, the anchor reload assembly 400 can be modified to accommodate multiple suture anchors 510. For example, the retention pin 486 can include multiple suture capture rods 492 each with a suture anchor 510 mounted thereto and the first and second halves 402 and 404 can be modified to accommodate the multiple capture rods 492.

The anchor reload assembly 400 can also be used to load multiple anchors at different points on a single suture. For example, multiple anchors can be loaded on a suture tail of a suture construct in a "daisy-chain" fashion.

Figure 22:
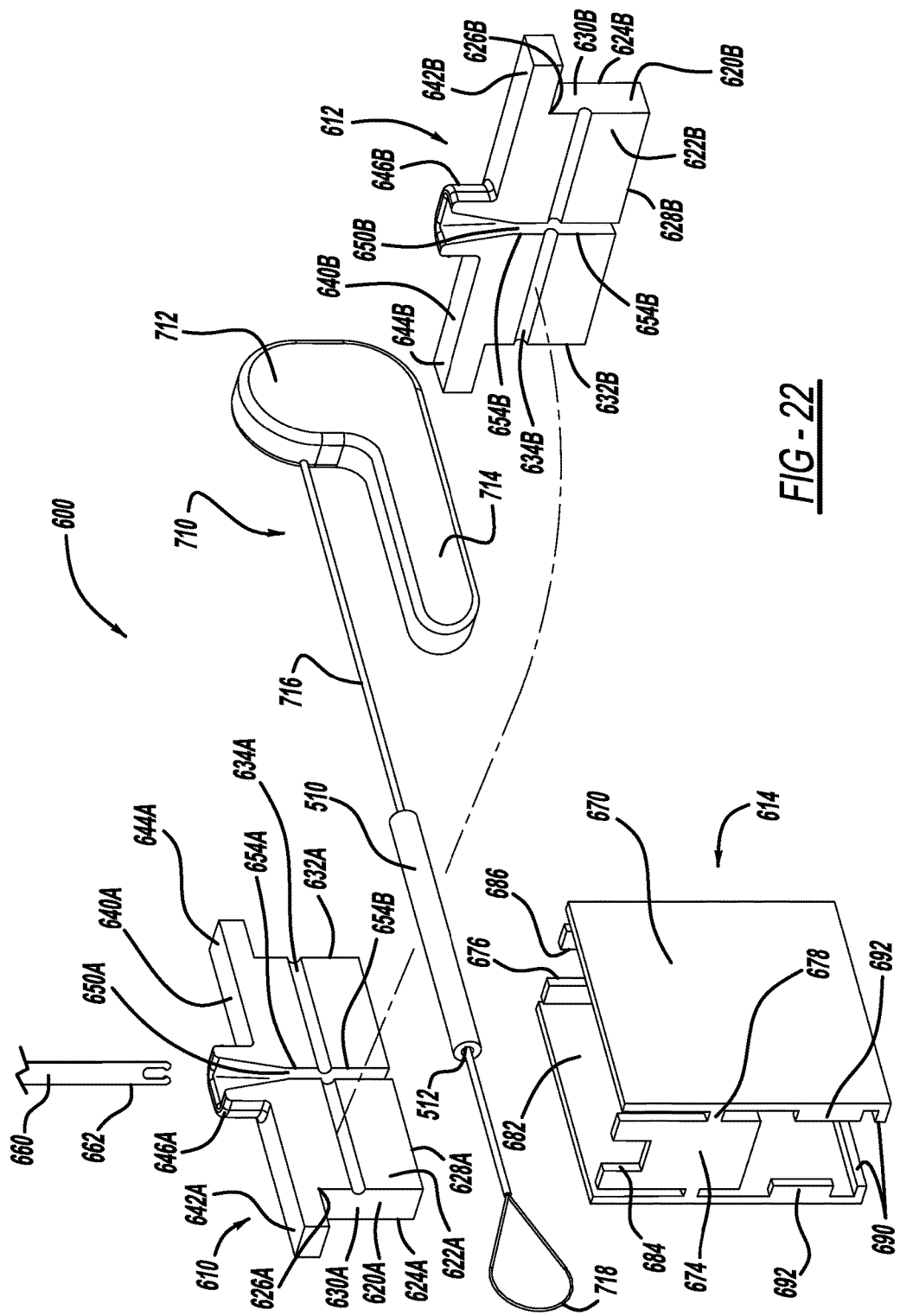
FIG. 22 is an exploded view of an additional suture anchor loading assembly according to the present teachings.
Figure 23:
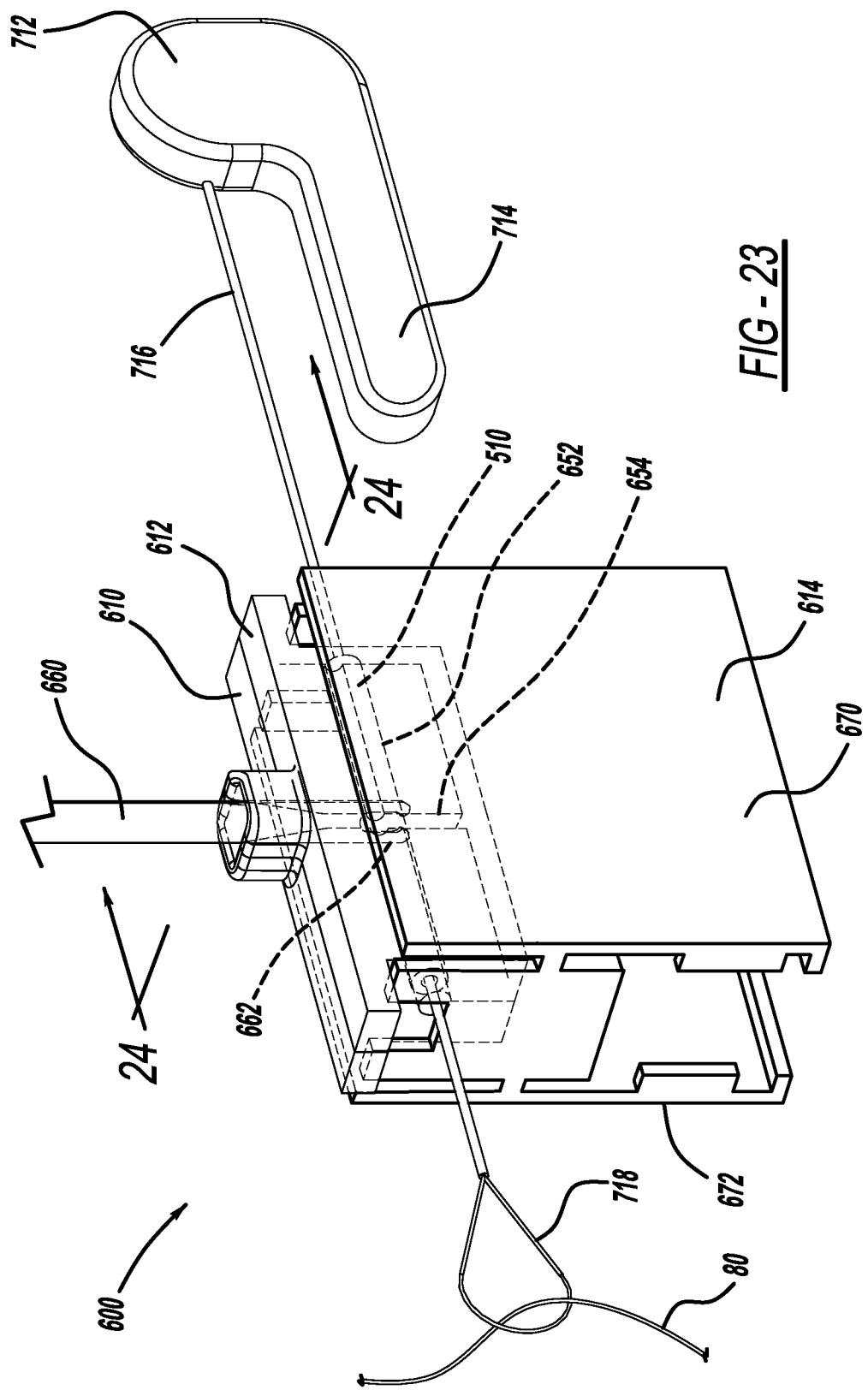
FIG. 23 is a perspective view of the suture anchor loading assembly of FIG. 22 with an inserter coupled to a suture anchor.
Figure 24:
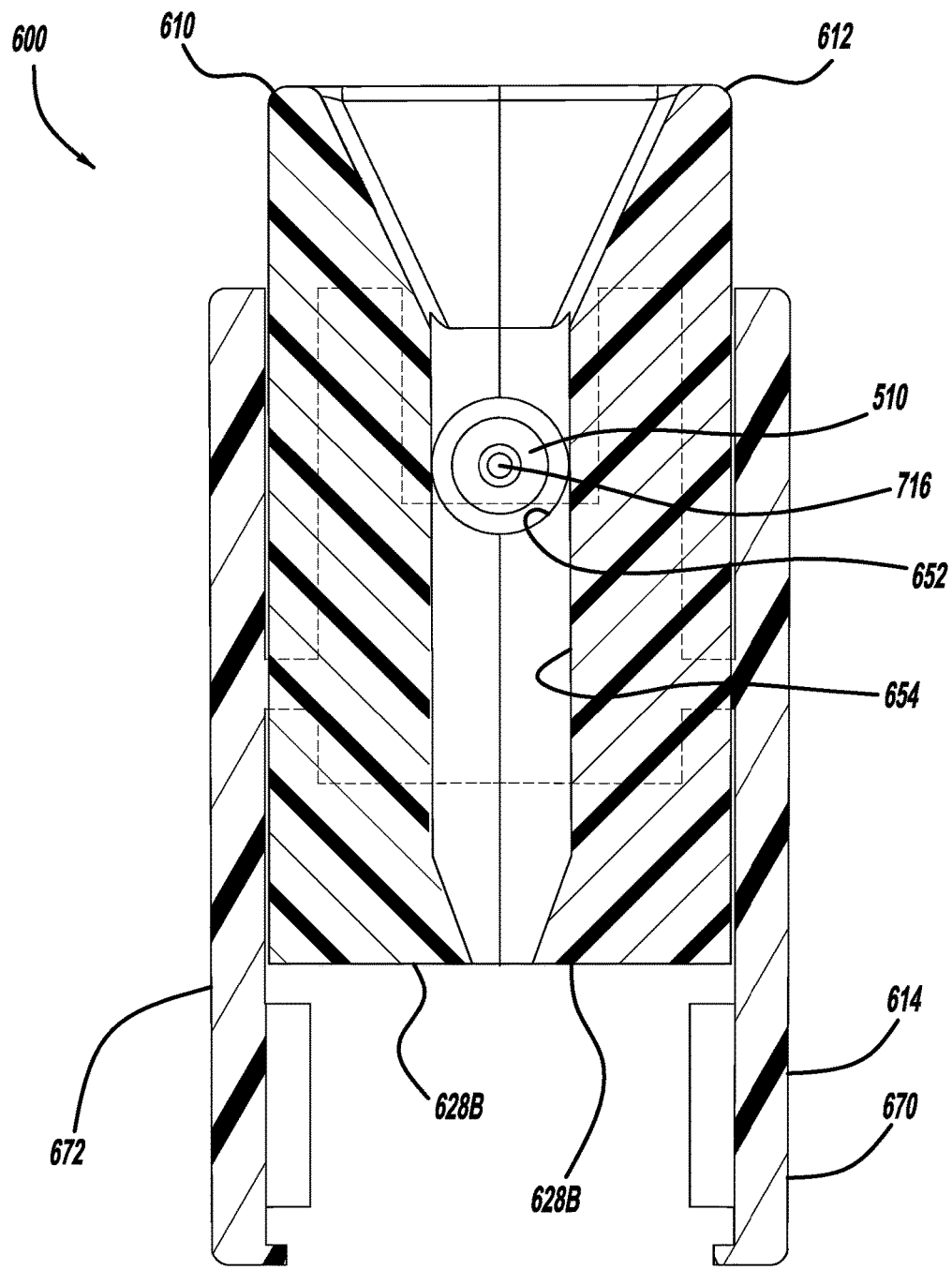
FIG. 24 is a cross-sectional view taken along line 24-24 of FIG. 23, without the inserter illustrated.

With reference to FIGS. 22-24, an additional suture anchor loading assembly according to the present teachings is generally illustrated at Reference 600. The suture anchor loading assembly 600 generally includes a first portion or first half 610, a second portion or second half 612, and a superstructure 614 configured to hold the first and the second portions 610 and 612 together. The first portion 610 and the second portion 612 are generally similar to one another, and can be mirror images of one another as illustrated. Features in common between the first and the second portions 610 and 612 are designated in the drawings using the same reference numerals, with the reference numerals assigned to the first portion 610 including the suffix "A," and reference numerals designating features of the second portion 612 including the suffix "B." The description of the first portion 610 set forth below also applies to the second portion 612 with respect to the like features.

The first portion 610 generally includes a main body 620A having an inner surface 622A and an outer surface 624A opposite thereto. The main body 620A further includes an upper portion 626A and a lower portion 628A opposite thereto. Extending between the upper and lower portions 626A and 628A is a first side surface 630A and a second side surface 632A. The first side surface 630A and the second side surface 632A are on opposite sides of the main body 620A.

The main body 620A defines a suture anchor cavity 634A extending across the main body 620A from the first side surface 630A to the second side surface 632A. The suture anchor cavity 634A of the first portion 610, and the suture anchor cavity 634B of the second portion 612, together define a suture anchor receptacle 652 when the first and the second portions are held together with the superstructure 614 (see FIG. 23, for example). The suture anchor cavity 634A and the suture anchor cavity 634B each define one-half of the suture anchor receptacle 652.

At the upper portion 626A of the main body 620A is a head portion 640A of the first portion 610. The head portion 640A extends across the upper portion 626A and includes a first shoulder or flange 642A, which extends beyond the first side surface 630A. A second shoulder or flange 644A of the head portion 640A extends beyond the second side surface 632A.

Extending from the head portion 640A, generally between the first and second shoulders 642A and 644A, is an inserter guide flange 646A. Extending through, and defined by, the inserter guide flange 646A, the head portion 640A, and the main body 620A is an inserter passageway or slot 650A. The inserter passageway 650A of the first portion 610 and an inserter passageway or slot 650B of the second portion 612 together define an inserter receptacle 654 (see FIG. 23, for example). The inserter passageways 650A and 650B each define one-half of the inserter receptacle 654.

The inserter passageways 650A and 650B extend through the inserter guide flange 646A, across the head portion 640A, and across the main body 620A, and thus the inserter receptacle 654 does as well. The inserter passageways 650A and 650B also extend across the suture anchor cavities 634A and 634B respectively. The inserter receptacle 654 thus extends across the suture anchor receptacle 652. The inserter receptacle 654 extends generally perpendicular to the suture anchor receptacle 652.

The inserter passageways 650A and 650B are keyed to receive an inserter 660 therein such that a hook 662 of the inserter 660 is oriented to couple with a suture anchor 510 seated in the suture anchor receptacle 652. The inserter receptacle 654 is thus keyed to orient the hook 662 as well. The inserter passageways 650A and 650B provide the inserter receptacle 654 generally with a first portion 654A and a second portion 654B. The first portion 654A extends generally between the inserter guide flange 646A and the suture anchor receptacle 652. The second portion 654B extends generally between the suture anchor receptacle 652 and the lower portion 628A of the main body 620A.

The first and second portions 654A and 654B are generally angled or tapered towards the inner surfaces 622A and 622B respectively such that the inserter receptacle 654 is generally deepest, and thus recessed furthest beneath the inner surfaces 622A and 622B, at the upper portions 626A and 626B. The inserter receptacle 654 is generally most shallow at the lower portions 628A and 628B (see FIG. 24, for example). Thus, the inserter receptacle 654 is generally tapered inward from the inserter guide flanges 646A/646B to the lower portions 628A/628B. Because the inserter receptacle 654 is tapered, insertion of the inserter 660 through the inserter receptacle 654 forces the first and second portions 610 and 612 apart when they are seated together in the superstructure 614, which forces the superstructure 614 to break apart.

The superstructure 614 generally includes a first side member 670 and a second side member 672 opposite thereto. The first and second side members 670 and 672 are coupled together with a first end panel 674 and with a second end panel 676. The first and second end panels 674 and 676 are coupled to the first and second side members 670 and 672 with coupling portions 678. The coupling portions 678 are generally narrow portions, which are generally weak frangible portions that can be relatively easily broken apart or severed when the inserter 660 is pushed through the inserter receptacle 654, thereby pushing the first and second portions 610 and 612 apart. The superstructure 614 generally defines a receptacle 682 configured to receive a first and second portion 610 and 612 therein.

The first end panel 674 defines a first aperture 684, and the second end panel 676 defines a second aperture 686. The first and second apertures 684 and 686 are generally aligned with the suture anchor receptacle 652 when the first and second portions are seated in the receptacle 682. The first and the second apertures 684 and 686 provide access to the suture anchor receptacle 652.

Figure 25:
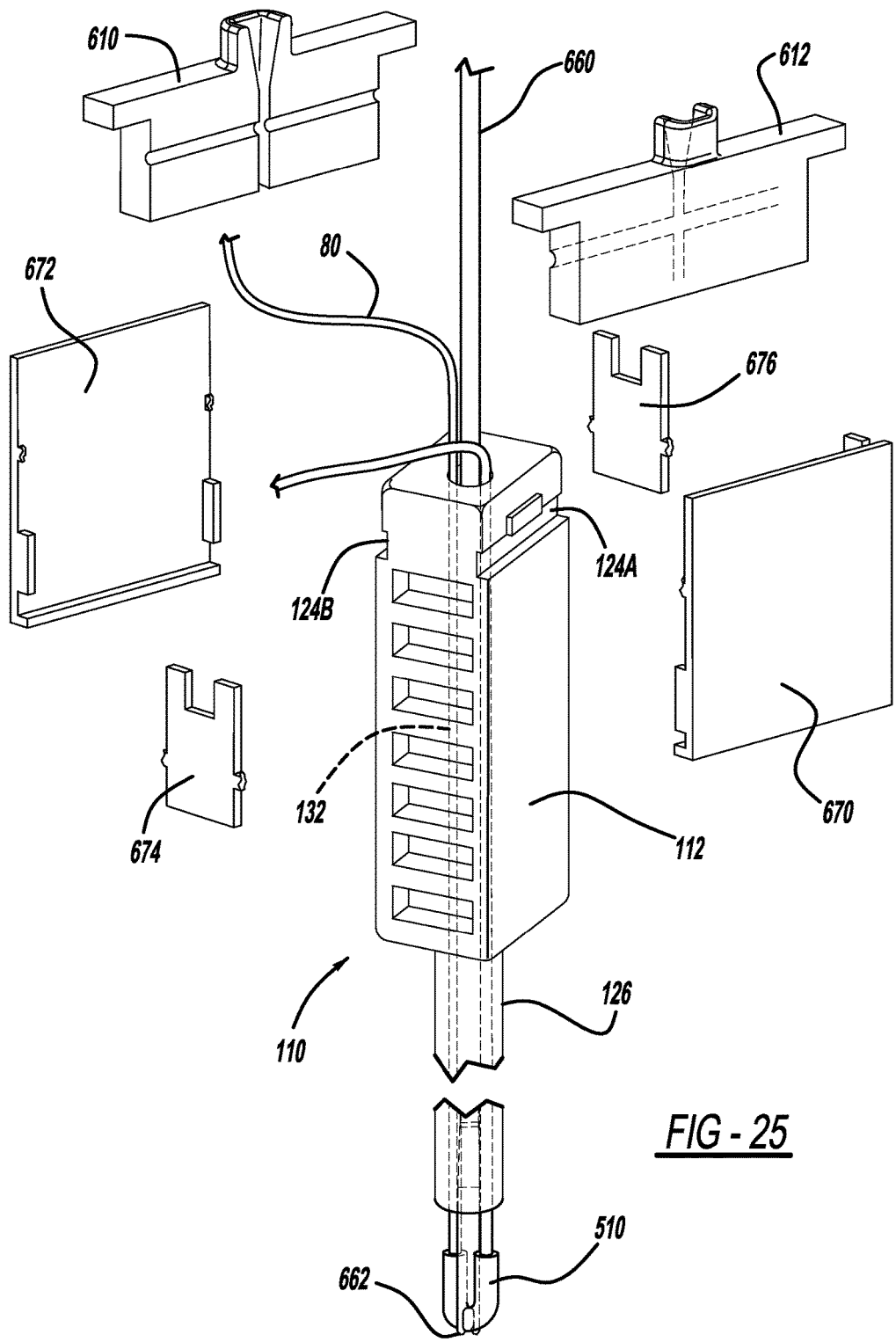
FIG. 25 illustrates the suture anchor loading assembly of FIG. 22 and an insertion cannula, the suture anchor loading assembly broken apart due to insertion of the inserter through the suture anchor loading assembly and into the insertion cannula.

With additional reference to FIG. 25, the superstructure 614 can be coupled to the insertion cannula 110 described above at the first and second slots 124A and 124B. Specifically, the superstructure 614 includes guide coupling flanges 690 and guide alignment flanges 692. The guide coupling flanges are configured to couple with the first and second slots 124A and 124B of the handle 112. The guide alignment flanges 692 are configured to center the superstructure 614 on the handle 112 such that the inserter receptacle 654 is aligned with the bore 132.

A suture anchor threading assembly is generally designated at reference 710. The suture anchor threading assembly 710 generally includes a handle 712, and may include an elongated portion 714 extending therefrom. Also extending from the handle 712 is a suture capture rod 716. At a distal end of the suture caption rod 716 is a suture capture portion 718, which can be a loop as illustrated. The suture capture rod 716 is configured such that the suture anchor 510 can be seated thereon, with the suture capture rod 716 extending through the interior 512 of the suture anchor 510.

Operation of the suture anchor loading assembly 600 to load the suture anchor 510 onto the suture 80 will now be described in detail. With the suture anchor 510 seated on the suture capture rod 716, the suture anchor 510 is positioned in the suture anchor cavity 634A of the first portion 610 and the suture anchor cavity 634B of the second portion 612 by pressing the first and second portion 610 and 612 together. Thus, the suture anchor 510 is seated in the suture anchor receptacle 652 defined by the suture anchor cavities 634A and 634B. To hold the first and second portions 610 and 612 together, they are seated within the receptacle 682 of the superstructure 614. Assembling the suture anchor loading assembly 600 in this manner can be performed by, for example, a manufacturer or by hospital staff. For example, a manufacturer may assemble the suture anchor loading assembly 600 in this manner, and after the original suture anchor 510 is implanted, hospital personnel may load another suture anchor 510 onto the suture 80, or a different suture 80, and reassemble the suture anchor assembly 600 as described above using a new, unbroken, superstructure 614. The first and second portions 610 and 612, as well as the suture anchor threading assembly 710, can thus be reused.

The suture 80 is then threaded through the suture capture portion 718. To hold the suture anchor 510 within the suture anchor receptacle 652, the inserter 660 is inserted into the inserter receptacle 654 such that the hook 662 of the inserter 660 engages and couples with the suture anchor 510. The handle 712 is then pulled in order to draw the suture capture portion 718 with the suture 80 extending therethrough out from within the suture anchor receptacle 652. This causes the suture capture portion 718 to pull the suture 80 through the interior 512 of the suture anchor 510 in order to thread the suture 80 through the suture anchor 510.

After the suture capture portion 718 has been pulled completely through the interior 512, and the suture 80 extends completely through the interior 512, the inserter 660 is pushed further through the inserter receptacle 654. Because the inserter receptacle 654 is tapered inward as described above and illustrated in FIG. 24, advancing the inserter 660 further through the inserter receptacle 654 pushes the first and second portions 610 and 612 apart, which forces the first and second side members 670 and 672 of the superstructure 614 apart and breaks the superstructure 614, generally at the coupling portions 678, as illustrated in FIG. 25, for example. The first and second portions 610 and 612 will then separate and generally fall away from the suture anchor 510, allowing the suture anchor 510 to be positioned using the inserter 660 as appropriate. If the superstructure 614 is coupled to the insertion cannula 110, the first and second portions will detach from the handle 112 as the inserter 660 is pushed through the inserter receptacle 654, thus allowing the inserter 660 to be advanced through the shaft 126 of the insertion cannula 110 in order to, for example, implant the suture anchor 510 in bone.

Another suture anchor 510 can be added or loaded onto the suture 80 using the suture anchor loading assembly 600 in the same manner described above. Therefore, multiple anchors 510 can be loaded onto the suture 80 in a "daisy-chain" fashion. The different suture anchors 510 can be implanted into different areas, such as different bone holes, as appropriate.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A suture anchor loading system fir loading a suture anchor on a suture, the suture anchor loading system comprising:
  a first portion and a second portion defining a suture anchor receptacle and an inserter receptacle therebetween, wherein the inserter receptacle is tapered inward from a proximal end to a distal end such that the first portion and the second portion are configured to be forced apart by movement of an inserter toward the distal end; and a superstructure configured to retain the first and the second portions together;

wherein the suture anchor can be loaded onto the suture when the suture anchor is seated within the suture anchor receptacle.

2. The suture anchor loading system of claim 1, further comprising the inserter for positioning the suture anchor at an implant site;

wherein the inserter receptacle is configured to receive the inserter.

3. The suture anchor loading system of claim 2, further comprising the suture anchor.

4. The suture anchor loading system of claim 2, wherein the inserter receptacle is keyed to orientate a hook portion of the inserter to couple with the suture anchor seated in the suture anchor receptacle.

5. The suture anchor loading system of claim 1, wherein each one of the first portion and the second portion includes a body and a head portion, the head portion including first and second flanges extending beyond side portions of the first and the second portions.

6. The suture anchor loading system of claim 1, wherein the first portion includes a first half of the suture anchor receptacle extending across the first portion, and the second portion includes a second half of the suture anchor receptacle extending across the second portion.

7. The suture anchor loading system of claim 1; wherein the first portion is a first half and the second portion is a second half that is a mirror-image of the first half.

8. The suture anchor loading system of claim 1, wherein the superstructure defines a receptacle configured to receive both the first portion and the second portion therein.

9. The suture anchor loading system of claim 1, further comprising a suture anchor threading assembly configured to draw the suture through the suture anchor, the suture anchor threading system including a handle, a suture capture rod configured to receive the suture anchor thereon, and a loop at a distal end of the suture capture rod;

wherein with the suture anchor seated on the suture capture rod and within the suture anchor receptacle, the loop is configured to be threaded with the suture such that upon pulling the suture capture rod out from within both the suture anchor receptacle and the suture anchor the suture is threaded through the suture anchor to position the suture anchor on the suture.

10. The suture anchor loading system of claim 1, wherein the inserter receptacle extends generally perpendicular to the suture anchor receptacle.

11. The suture anchor loading system of claim 2, further comprising a cannulated insertion guide;

wherein the superstructure is configured to couple with the cannulated insertion guide; and wherein upon insertion of the inserter into the inserter receptacle to capture the suture anchor seated within the suture anchor receptacle and push the suture anchor into the cannulated insertion guide, the inserter forces the first portion and the second portion apart to break the superstructure.

12. A suture anchor loading assembly for loading a suture anchor on a suture, the suture anchor loading assembly comprising:

a first portion and a second portion defining a suture anchor receptacle and an inserter receptacle therebetween, the suture anchor receptacle intersects the inserter receptacle, the inserter receptacle is tapered inward such that the inserter receptacle is narrower on a distal side of the suture anchor receptacle than on a proximal side of the suture anchor receptacle, such that insertion of an inserter through the inserter receptacle would separate the first and second portions;

a superstructure defining a receptacle configured to receive the first and the second portions therein and retain the first and the second portions together; and a suture anchor threading assembly including: a handle; a suture capture rod configured to receive the suture anchor thereon; and a suture capture portion;

wherein with the suture capture rod having the suture anchor thereon seated within the suture anchor receptacle, and an inserter seated in both the inserter receptacle and the suture anchor receptacle such that the inserter is coupled to the suture anchor, withdrawal of the suture anchor threading assembly out from within the suture anchor receptacle pulls the suture capture portion with the suture coupled thereto through the suture anchor to thread the suture through the suture anchor.

13. The suture anchor loading assembly of claim 12, further comprising the inserter.

14. The suture anchor loading assembly of claim 12, wherein insertion of the inserter through the inserter receptacle breaks the superstructure.

15. A method for loading a suture anchor onto a suture using a suture anchor loading assembly including a first portion and a second portion defining therebetween a suture anchor receptacle and an inserter receptacle intersecting the suture anchor receptacle, the inserter receptacle tapered inward from a proximal end to a distal end, the first and the second portions contained within a superstructure, the method comprising:

inserting an inserter into the inserter receptacle and into the suture anchor receptacle to couple the inserter with the suture anchor;

coupling the suture to a suture capture portion of a suture capture rod;

withdrawing the suture capture rod out from within the suture anchor receptacle to thread the suture through the suture anchor; and advancing the inserter further into the inserter receptacle from the proximal end to the distal end to force the first portion and the second portion apart and break the superstructure.

16. The method of claim 15, further comprising:

arranging a suture capture rod of a suture anchor threading assembly between the first and the second portions such that a suture anchor seated on the suture capture rod is within the suture anchor receptacle; and positioning the first portion and the second portion within a superstructure receptacle defined by a superstructure to hold the first portion and the second portion together.

17. The method of claim 16, further comprising coupling the superstructure to a cannulated insertion guide such that the inserter receptacle is aligned with a cannula of the cannulated insertion guide, and passing the inserter through the inserter receptacle into the cannula.

18. The method of claim 17, further comprising separating the superstructure from the cannulated insertion guide by advancing the inserter through the inserter receptacle to break the superstructure.

19. The method of claim 18, further comprising passing the suture anchor through the cannula of the inserter and into a first bone hole to implant the suture anchor in the first bone hole.

20. The method of claim 19, wherein the suture anchor is a first suture anchor, the method further comprising: loading a second suture anchor onto the suture and implanting the second suture anchor into a second bone hole of the bone.

* * * * *

UNITED STATES PATENT AND TRADEMARK OFFICE
CERTIFICATE OF CORRECTION

PATENT NO. : 10,052,092 B2
APPLICATION NO. : 14/489695
DATED : August 21, 2018
INVENTOR(S) : Finley et al.

Page 1 of 1

It is certified that error appears in the above-identified patent and that said Letters Patent is hereby corrected as shown below:

On the Title Page

On page 2, in Column 2, under "Other Publications", Line 33, delete "Labial" and insert --Labral-- therefor In the Claims In Column 18, Line 61, in Claim 1, delete "fir" and insert --for-- therefor In Column 19, Line 30, in Claim 7, delete "claim 1;" and insert --claim 1,-- therefor Signed and Sealed this
Eleventh Day of June, 2019

Andrei Iancu
*Director of the United States Patent and Trademark Office*